(12) United States Patent
Bashore et al.

(10) Patent No.: US 7,122,203 B2
(45) Date of Patent: Oct. 17, 2006

(54) STABILIZED FORMULATIONS OF 6-HYDROXY-3-(-4-[2-(PIPERIDIN-1-YL) ETHOXY]PHENOXY)-2-(4-METHOXYPHENYL) BENZO[B]THIOPHENE AND SALTS THEREOF

(75) Inventors: Fadia Najjar Bashore, Indianapolis, IN (US); Kerry John Hartauer, Carmel, IN (US); Michael Dean Minnett, Greenwood, IN (US); Eugene Clark Rickard, Zionsville, IN (US); Cheryl Ann Tingle, Mooresville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 587 days.

(21) Appl. No.: 10/258,273

(22) PCT Filed: Apr. 30, 2001

(86) PCT No.: PCT/US01/11736

§ 371 (c)(1),
(2), (4) Date: Oct. 18, 2002

(87) PCT Pub. No.: WO01/85147

PCT Pub. Date: Nov. 15, 2001

(65) Prior Publication Data

US 2003/0119875 A1 Jun. 26, 2003

Related U.S. Application Data

(60) Provisional application No. 60/203,235, filed on May 8, 2000.

(51) Int. Cl.
*A61K 9/20* (2006.01)
(52) U.S. Cl. .................... 424/464; 424/451
(58) Field of Classification Search .............. None
See application file for complete search history.

(56) References Cited

U.S. PATENT DOCUMENTS

| | | | |
|---|---|---|---|
| 5,114,948 A | 5/1992 | Conine et al. | 514/288 |
| 5,723,474 A | 3/1998 | Palkowitz | 514/324 |
| 5,811,120 A | 9/1998 | Gibson et al. | 424/464 |
| 6,610,706 B1 * | 8/2003 | Bush et al. | 514/324 |
| 6,653,479 B1 * | 11/2003 | Bush et al. | 546/202 |

FOREIGN PATENT DOCUMENTS

| | | |
|---|---|---|
| GB | 2 352 716 A | 2/2001 |
| WO | WO01/09115 | 2/2001 |
| WO | WO01/09116 | 2/2001 |

* cited by examiner

*Primary Examiner*—Gollamudi S. Kishore
*Assistant Examiner*—Pili A. Hawes
(74) *Attorney, Agent, or Firm*—MaCharri Vorndran-Jones

(57) ABSTRACT

The present invention is directed to pharmaceutical formulations containing 6-hydroxy-3-(4-[2-(piperidin-1-yl) ethoxy]phenoxy)-2-(4-methoxypheny)benzo[b]thiophene or a salt thereof; stabilized to oxidation or other forms of decomposition by incorporation of a stabilizing agent selected from methionine, acetylcysteine, cysteine or salts thereof.

39 Claims, 12 Drawing Sheets

A) S-II initially.
B) S-II after vacuum drying at 100°C for 22 hours.
C) S-II after vacuum drying at 100°C for 47 hours.
D) S-II after vacuum drying at 100°C for 118 hours.

STABILIZED FORMULATIONS OF 6-HYDROXY-3-(-4-[2-(PIPERIDIN-1-YL) ETHOXY]PHENOXY)-2-(4-METHOXYPHENYL) BENZO[B]THIOPHENE AND SALTS THEREOF

This is the national phase application, under 35 USC 371, for PCT/US01/11736, filed 30 Apr. 2001, which claims the priority of U.S. provisional application No. 60/203,235, filed 8 May 2000.

BACKGROUND OF THE INVENTION

6-Hydroxy-3-(4-[2-(piperidin-1-yl)ethoxy]phenoxy)-2-(4-methoxyphenyl)benzo[b]thiophene hydrochloride (arzoxifene hydrochloride) was first described generically in U.S. Pat. No. 5,510,357 ('357) and was specifically disclosed in U.S. Pat. No. 5,723,474 ('474). Both the '357 and '474 patents are incorporated herein by reference. Arzoxifene, whether in its free base or salt form, is a nonsteroidal mixed estrogen antagonist/agonist, useful for, inter alia, lowering serum cholesterol and for inhibiting hyperlipidemia, osteoporosis, estrogen dependent cancers including breast and uterine cancer, endometriosis, CNS disorders including Alzheimer's disease, aortal smooth muscle cell proliferation, and restenosis. The compound is currently undergoing clinical evaluation for the treatment and prevention of osteoporosis and the treatment of endometrial and breast cancer in women. Specifically, arzoxifene is useful for, and is being clinically evaluated for the treatment of receptor positive metastatic breast cancer; the adjuvant treatment of receptor positive patients following appropriate local or systemic therapy; the reduction of recurrence of invasive and noninvasive breast cancer; the reduction of the incidence of invasive breast cancer and ductal carcinoma in situ ("DCIS"). Arzoxifene is also useful in combination with radiotherapy; aromatase inhibitors, such as Aminoglutemide (CYTANDREN®), Anastrazole (ARIMIDEX®), Letrozole (FEMARA®), Formestane (LENATRON®), Exemestane (AROMASIN®), and the like; LHRH analogues, such as Goserlin (ZOLADEX®), Leuprolide (LUPRON®), and the like; and acetylcholinesterase inhibitors.

Arzoxifene is known to decompose over time as evidenced by the formation of degradation products, particularly an N-oxide degradation product and a cleavage degradation product. The formation of degradation products of an active pharmaceutical ingredient is typically undesirable. Such degradation products have the potential of untoward side effects and unnecessary exposure of the patients. The control of degradation products or impurities is regulated by International Conference on Harmonisation (ICH) guidelines as implemented by national regulatory authorities such as the United States Food and Drug Administration (FDA). The ICH guidelines delineate levels of such degradation products or impurities above which structural identification and qualification by appropriate toxicological or clinical studies must be performed.

Initial attempts at reducing the formation of degradation products of arzoxifene in a pharmaceutical composition were unsuccessful. The incorporation of the classical antioxidant molecule (ascorbic acid) actually augmented the formation of arzoxifene N-oxide degradation product, as well as the formation of other degradation products, with higher levels immediately after manufacture and a greater rate of increase during storage. As indicated in the pharmaceutical literature (see Akers M. J., *Journal of Parenteral Science and Technology*, 36(5):222–227 (1982)) there is no reliable method for predicting the effectiveness of antioxidant activity in pharmaceutical products.

We have now discovered that the addition of a stabilizing agent selected from methionine, acetylcysteine, cysteine or salts thereof as part of the pharmaceutical composition of arzoxifene tablets will greatly reduce the formation of degradation products during the manufacturing process and/or storage of the drug product.

BRIEF SUMMARY OF THE INVENTION

Figure 1:
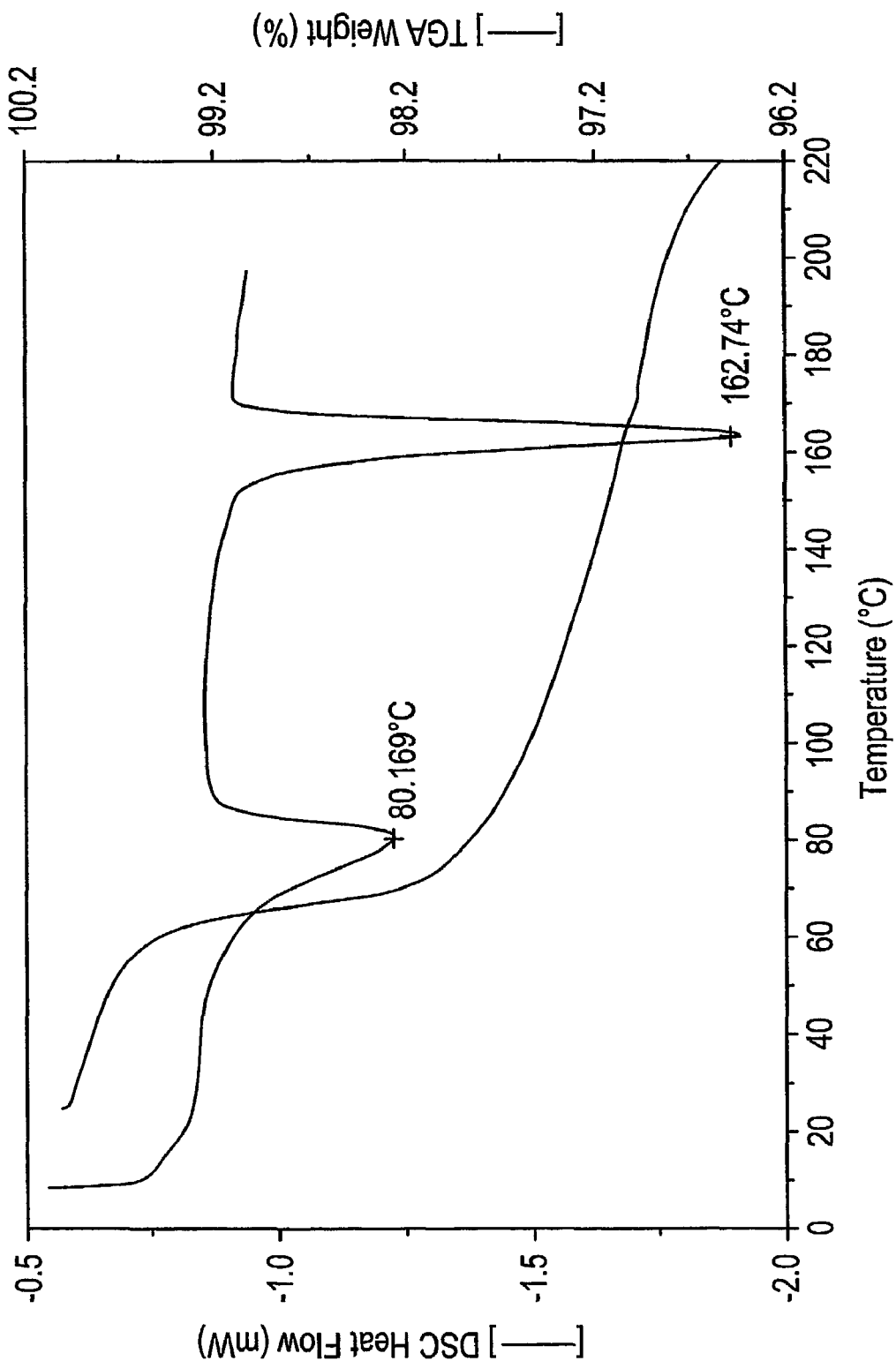
FIG. 1 is a representative differential scanning calorimetry (DSC)/thermogravimetric analysis (TGA) trace of S-II.

The present invention is directed to a pharmaceutical formulation comprising 6-hydroxy-3-(4-[2-(piperidin-1-yl)ethoxy]phenoxy)-2-(4-methoxyphenyl)benzo[b]thiophene or a salt thereof; a stabilizing agent selected from methionine, acetylcysteine, cysteine or salts thereof in an amount sufficient to effect stabilization to decomposition; and pharmaceutically acceptable excipients.

Also disclosed is a method of stabilizing a pharmaceutical formulation of 6-hydroxy-3-(4-[2-(piperidin-1-yl)ethoxy]phenoxy)-2-(4-methoxyphenyl)benzo[b]thiophene or a salt thereof to decomposition during the manufacturing process or storage of the drug product. The method comprises incorporating into said pharmaceutical formulation, in addition to a therapeutically effective amount of said 6-hydroxy-3-(4-[2-(piperidin-1-yl)ethoxy]phenoxy)-2-(4-methoxyphenyl)benzo[b]thiophene or a salt thereof and one or more pharmaceutical carriers, diluents, or excipients, a stabilizing agent selected from methionine, acetylcysteine, cysteine or salts thereof in an amount sufficient to effect stabilization to decomposition.

Further disclosed is a method for inhibiting a pathological condition selected from the group consisting of: uterine fibrosis, endometriosis, aortal smooth muscle cell proliferation, restenosis, breast cancer, uterine cancer, prostatic cancer or benign prostatic hyperplasia, bone loss, osteoporosis, cardiovascular disease, hyperlipidemia, CNS disorders, and Alzheimer's disease; which comprises administering to a mammal in need thereof, an effective amount of the pharmaceutical formulation disclosed herein.

Additionally, stabilized pharmaceutical formulations containing the F-I, F-III or F-V crystalline forms of arzoxifene hydrochloride are disclosed.

DETAILED DESCRIPTION OF THE INVENTION

Arzoxifene (i.e. 6-hydroxy-3-(4-[2-(piperidin-1-yl) ethoxy]phenoxy)-2-(4-methoxyphenyl)benzo[b]thiophene) and salts thereof may be prepared as described in U.S. Pat. No. 5,510,357 ('357) and U.S. Pat. No. 5,723,474 ('474), both of which are incorporated herein by reference as if fully set forth.

Bulk arzoxifene hydrochloride prepared by the procedure taught in '474 (Example 41, crystallization from a mixture of ethanol and ethyl acetate, filtration and drying of the filter cake in vacuo to a constant weight at room temperature) was characterized by XRD and was found to be poorly crystalline. $^1$H NMR confirmed that the bulk material contained 6% ethyl acetate.

The crystallization procedure taught in '474 was subsequently modified so that ethanol was added to a suspension of crude arzoxifene hydrochloride in refluxing ethyl acetate. Upon cooling and vacuum filtration, the solid that results from this modified procedure is a highly crystalline mixed ethyl acetate/water solvate of arzoxifene hydrochloride (hereinafter referred to as S-II) which was later discovered to be the starting material for F-I (another crystalline form of arzoxifene hydrochloride).

F-I is prepared by removing the ethyl acetate from S-II's crystal lattice by vacuum drying/annealing S-II at elevated temperatures. The time and temperature required to anneal S-II in order to prepare F-I will vary from lot to lot but is typically on the order of 5 days at around 100° C. High temperatures are needed to effect the conversion of S-II to F-I, since slurrying S-II in water at ambient temperature or storing a sample at 98% relative humidity (R.H.) for 3 weeks afforded no conversion to F-I. Furthermore, drying S-II in a convection oven at high temperatures did not de-solvate the material either, suggesting that a vacuum is also required to pull the ethyl acetate from S-II's lattice.

A preferred form of arzoxifene hydrochloride is F-III. F-III is readily prepared and isolated at ambient temperature. An advantage of F-III is that only moderate drying conditions are required to remove low levels of residual crystallization solvent. These moderate drying conditions consistently result in a solid of high purity and crystallinity and, thus, use of F-III eliminates toxicology issues associated with residual and crystal lattice organic solvent. Furthermore, preparation of F-III is simple and efficient, i.e., is amenable to bulk manufacture.

F-III is readily prepared and isolated at ambient temperature by crystallization of arzoxifene hydrochloride (or any polymorph/solvate thereof) from a mixture of isopropyl alcohol (IPA) and water. Typically, arzoxifene hydrochloride may be suspended in a mixture of IPA and water and heated in order to effect dissolution of the arzoxifene hydrochloride starting material. Once dissolution is achieved, the solution is allowed to cool slowly to room temperature and then further (with the aid of an ice bath or refrigeration) to between 0 and 5° C. After a sufficient amount of time has elapsed for crystallization to occur, the crystals may be collected by vacuum filtration and dried to a constant weight in vacuo to obtain F-III.

Suitable arzoxifene hydrochloride starting material for the above crystallization includes, but is not limited to, S-II, F-I, arzoxifene hydrochloride prepared by the procedures taught in '474, or any mixture thereof. It is not important which form of arzoxifene hydrochloride one starts with because crystallization from IPA and water, according to the procedures described herein, results in F-III crystals. The ratio of water to IPA (v:v) is generally about 1:1 to 5:1. More preferably, the ratio is between 2.5 and 3.5:1. Most preferably, the ratio is between 2.9 to 3.1:1. The ratio of IPA to water is not critical to effect crystallization of F-III but does affect the yield. Preferably, upon collection of the crystals by vacuum filtration, the F-III wet cake is washed with cold deionized water before drying in vacuo. In addition, slightly elevated drying temperatures (about 50° C. for 12 to 24 hours) are preferred. For commercial scale synthesis of F-III, it may be advantageous to seed the crystallization with F-III.

In a preferred process, F-III is prepared, isolated, and purified contiguous with the chemical removal of the 6-isopropyl hydroxy protecting group from 6-isopropoxy-3-(4-[2-(piperidin-1-yl)ethoxy]phenoxy)-2-(4-methoxyphenyl)benzo[b]thiophene hydrochloride (precursor A). The deprotection reaction is monitored for complete removal of the isopropyl protecting group and once it is determined that the removal is substantially complete, the work-up of the reaction will preferably include a crystallization under the conditions that provide F-III as discussed above and below. Methods for preparing precursor A and for removing the isopropyl group may be found in U.S. Pat. No. 5,723,474, the teachings of which are herein incorporated by reference.

In another preferred process, F-III is prepared, isolated and purified contiguous with the chemical reduction of the S-oxide and chemical removal of the benzyl protecting group from the 6-hydroxyl in 6-benzyloxy-3-(4-[2-(piperidin-1-yl)ethoxy]phenoxy)-2-(4-methoxyphenyl)benzo[b]thiophene-(S-oxide) (precursor B). The reduction and deprotection reactions are monitored for complete reduction of the sulfoxide to the sulfide and complete removal of the benzyl hydroxy protecting group. Once it is determined that the reduction/removal is substantially complete, the work-up of the reaction will preferably include a crystallization under the conditions that provide F-III as discussed herein. Methods for preparing precursor B, for removing the benzyl group, and for reducing the 1-sulfoxide to the corresponding sulfide may also be found in the previously incorporated by reference U.S. Pat. No. 5,723,474.

Irrespective of the chemistry utilized in the deprotection and reduction steps, crystallization of arzoxifene hydrochloride from an isopropyl alcohol/water solution consistently produces F-III crystals in high purity.

Another preferred form of arzoxifene hydrochloride is F-V. F-V may be prepared by drying, either at ambient temperature or at slightly elevated temperature, the crystalline solid isolated at ambient temperature from crystallization of arzoxifene hydrochloride (or any polymorph/solvate thereof) from methanol, ethanol or isopropanol or aqueous mixtures of methanol. When using ethanol or isopropanol, the water content in said solvents is preferably less than 0.2% (A.C.S. spectrophotometric grade). Preferably the aqueous composition in methanol contains less than 30% by volume water. More preferably F-V is prepared by drying, either at ambient temperature or at slightly elevated temperature, the solid isolated from crystallization from aqueous methanol wherein the volume of water is between 20% and 5%. Most preferably F-V is prepared by drying at 50 to 70° C., under vacuum, the solid isolated at ambient temperature from crystallization of arzoxifene hydrochloride (or any polymorph/solvate thereof) from aqueous methanol wherein the water content by volume is 15%.

Typically, arzoxifene hydrochloride may be dissolved in methanol (about 1 g solute/20 ml of solvent) and optionally heated in order to effect dissolution of the arzoxifene hydrochloride starting material. Once dissolution is achieved, the solution may optionally be concentrated to about 1 g of solute/5 ml of solvent, e.g., by distillation, before allowing the solution to cool slowly to room temperature. Once at room temperature, the solution may optionally be cooled further (with the aid of an ice bath or refrigeration) to between 0 and 5° C. After a sufficient amount of time has elapsed for crystallization to occur, the F-V crystals may be collected by vacuum filtration and washed with cold (about 0° C.) methanol before drying to a constant weight in vacuum. Slightly elevated drying temperatures (about 50° C. for 12 to 48 hours) in the presence of a nitrogen purge are preferred. For commercial scale synthesis of F-V, it may be advantageous to seed the crystallization with F-V.

Suitable arzoxifene hydrochloride starting material for the above crystallization includes, but is not limited to, S-II, F-I, F-III (solvated and non-stoichiometric hydrated crystalline forms of arzoxifene hydrochloride described in PCT Patent Applications PCT/US00/16332 and PCT/US00/16333, the teachings of which are hereby incorporated by reference), arzoxifene hydrochloride prepared by the procedures taught in '474, or any mixture thereof. It is not important which form of arzoxifene hydrochloride one starts with because crystallization from anhydrous methanol, according to the procedures described herein, results in F-V crystals.

Characterization and Differentiation of S-II, F-I, F-III, and F-V

DSC/TGA, moisture sorption/desorption and XRD methods were used to characterize S-II, F-I, F-III and F-V. TGA is often very useful for distinguishing between different solid forms of a material because the temperature(s) at which a physical change in a material occurs is usually characteristic of the polymorph or solvate. DSC is a technique that is often used to screen compounds for polymorphism and solvate formation. Moisture sorption isotherms provide evaluation of the degree of hygroscopicity associated with a given material and characterization of non-hydrates and hydrates. Lastly, XRD is a technique that detects long-range order in a crystalline material.

Arzoxifene hydrochloride prepared by the procedures taught in '474 gave XRD patterns with poor signal-to-noise ratios and a raised baseline, indicative of poorly crystalline material. Therefore, comparisons of F-I and F-III are made to the material (S-II) produced by the modified arzoxifene hydrochloride crystallization procedure discussed above (addition of ethanol to a suspension of arzoxifene hydrochloride in refluxing ethyl acetate).

Figure 2:
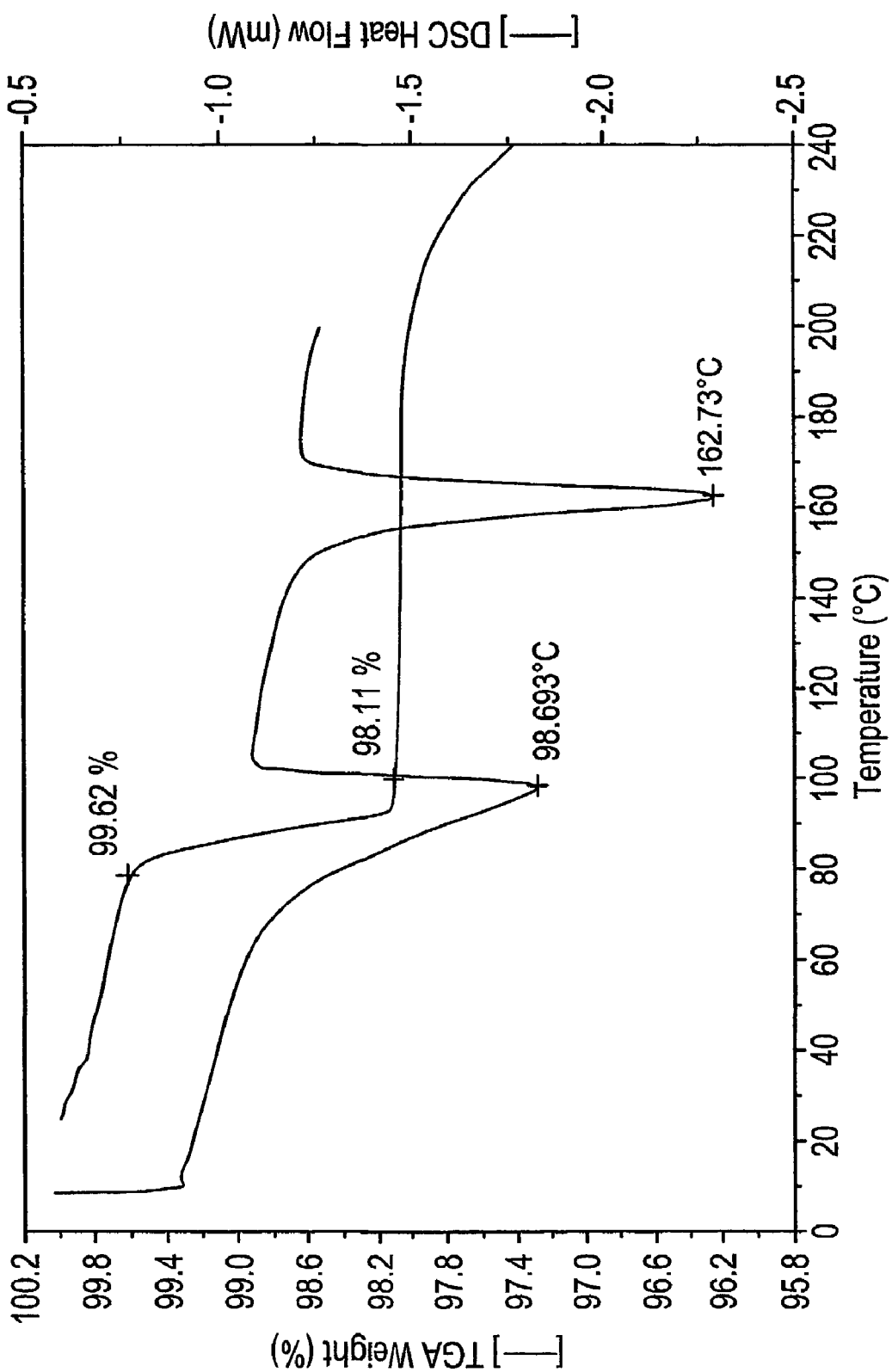
FIG. 2 is a representative DSC/TGA trace of F-I.
Figure 3:
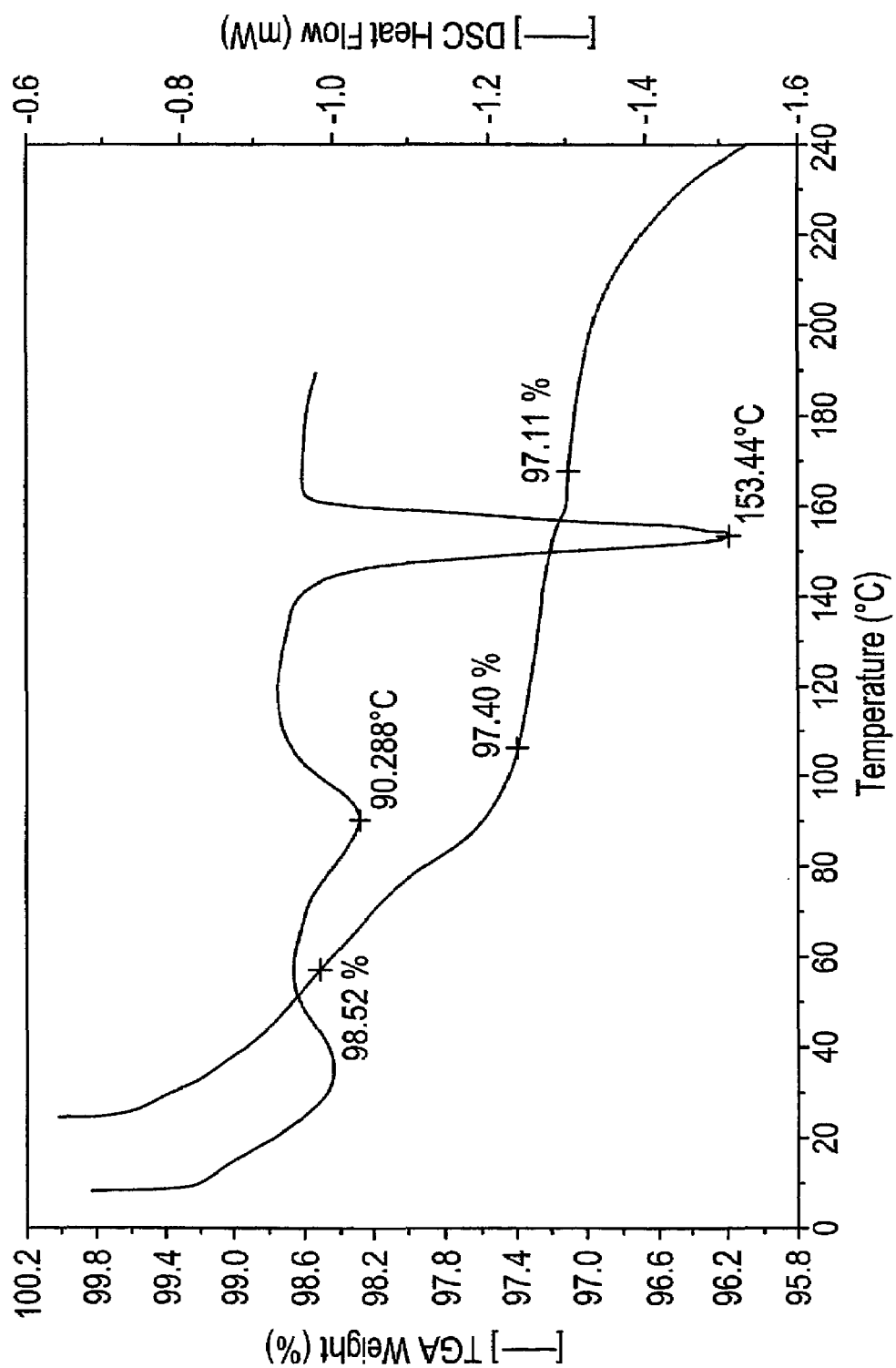
FIG. 3 is a representative DSC/TGA trace of F-III.

Representative DSC/TGA traces of S-II, F-I and F-III are shown in FIGS. 1, 2 and 3, respectively. The DSC trace for S-II shows a broad endotherm at 62° C., corresponding to the loss of ethyl acetate and water from the lattice. The endotherm at 152° C. represents a melt. The TGA weight loss of approximately 2.5% occurs simultaneous with the first transition, while the remaining 0.5% weight loss occurs up to the onset of melting, suggesting that some solvent molecules are more tightly held in the lattice.

The DSC trace of F-I shows a broad endotherm at 75° C., followed by a second endotherm at 155° C. corresponding to a melt. The TGA trace of F-I shows a gradual weight loss of 0.3% followed by a sharp loss of 1.5%, which together represent dehydration of the lattice. The onset of the first DSC transition and the corresponding TGA weight loss are offset slightly due to the difference in heating rates. The initial weight loss represents weakly held waters of hydration while the second weight loss is consistent with approximately 0.5 mole of water present in the lattice at very low relative humidities (below 5%—see moisture sorption data).

The DSC trace of F-III features a broad, low temperature endotherm at 30° C., followed by a second broad and relatively weak endotherm at 70° C., and a final transition at 146° C. corresponding to a melt. The sharp 1.5% (~0.5 mole) weight loss in the TGA coincident with the first endotherm corresponds to loss of weakly held water molecules, while the additional ~1.6% weight loss above 60° C. represents loss of more tightly held water molecules, i.e., those which are present at very low relative humidities. The weight loss observed after 170° C. corresponds to decomposition of F-III.

Figure 4:
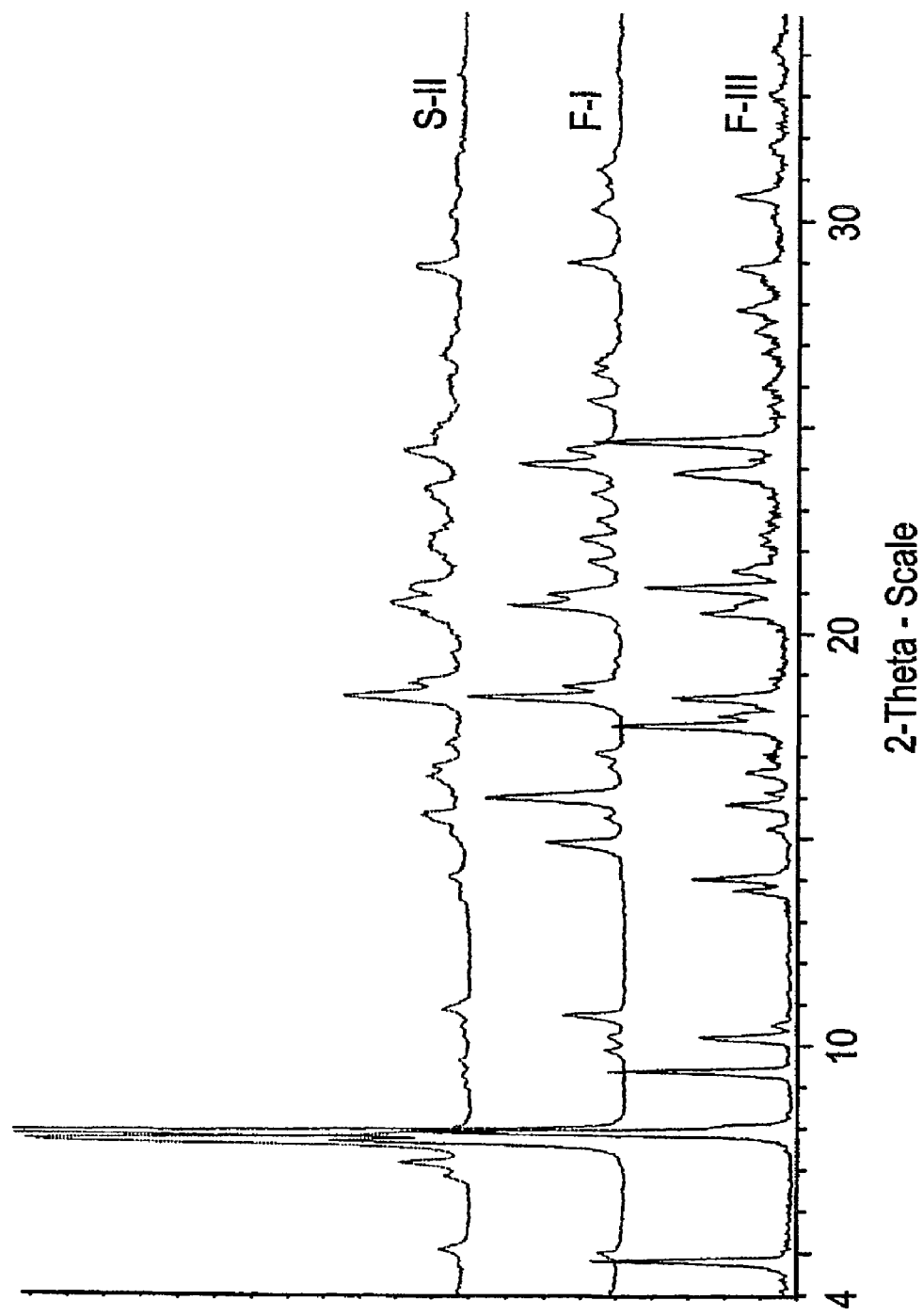
FIG. 4 depicts a X-ray powder diffraction (XRD) pattern for F-III taken at 25±2° C. and 35±10% relative humidity, and the XRD patterns for S-II and F-I.

An XRD pattern for F-III taken at 25±2° C. and 35±10% R.H. and the XRD patterns for S-II and F-I are shown in FIG. 4. The XRD patterns of F-I and F-III feature sharp peaks and a flat baseline, indicative of highly crystalline materials. The corresponding d line spacing and $I/I_o$ data is tabulated in Table 1. Although many of the intense reflections are generally at similar diffraction angles, each of the forms gives a different powder pattern, allowing for a clear distinction between S-II, F-I and F-III.

It is well known in the crystallography art that, for any given polymorph, the relative intensities of the diffraction peaks may vary due to preferred orientation resulting from factors such as crystal morphology. Where the effects of preferred orientation are present, peak intensities are altered, but the characteristic peak positions of the polymorph are unchanged. See, e.g., The United States Pharmacopeia #23, National Formulary #18, pages 1843–1844, 1995. Furthermore, it is also well known in the crystallography art that, for any given crystalline form, the angular peak positions may vary slightly. For example, peak positions can shift due to a variation in the temperature at which a sample is analyzed, sample displacement, or the presence or absence of an internal standard. In the present case, a peak position variability of ±0.2 in 2θ will take into account these potential variations without hindering the unequivocal identification of F-I, F-III or F-V.

Thus, based on peak intensities as well as peak position, F-III may be identified by the presence of peaks at 4.63±0.2, 7.82±0.2, 9.29±0.2, 13.97±0.2, 17.62±0.2, 20.80±0.2, and 24.31±0.2° in 2θ; when the pattern is obtained at 25±2° C. and 35±10% relative humidity from a copper radiation source.

A well known and accepted method for searching crystal forms in the literature is the "Fink" method. The Fink method uses the four most intense lines for the initial search followed by the next four most intense lines. In accord with the Fink method, based on the peak intensities as well as peak position, F-V may be identified by the presence of peaks at 7.3±0.2, 15.5±0.2, 15.9±0.2, and 17.6±0.2° in 2θ; when the pattern is obtained from a copper radiation source. The presence of F-V may be further verified by peaks at 17.9±0.2, 18.2±0.2, 18.9±0.2, and 21.5±0.20 in 2θ; when the pattern is obtained from a copper radiation source.

TABLE 1

| S-II | | F-I | | F-III | |
| --- | --- | --- | --- | --- | --- |
| d (°2θ) | $I/I_o$ (%) | d (°2θ) | $I/I_o$ (%) | d (°2θ) | $I/I_o$ (%) |
| 4.67 | 1.3 | 4.92 | 2.6 | 4.63 | 20.8 |
| 5.03 | 6 | 7.69 | 34.6 | 7.82 | 100 |
| 6.83 | 5.8 | 7.91 | 100 | 9.29 | 16.9 |
| 7.17 | 16.1 | 9.89 | 2.5 | 10.16 | 22.7 |
| 7.73 | 100 | 10.22 | 2 | 10.35 | 5.4 |
| 9.03 | 1.3 | 10.74 | 7.4 | 13.77 | 10.7 |
| 9.31 | 1.7 | 14.86 | 9.1 | 13.97 | 15.2 |

TABLE 1-continued

| S-II | | F-I | | F-III | |
|---|---|---|---|---|---|
| d (°2θ) | I/I$_o$ (%) | d(°2θ) | I/I$_o$ (%) | d(°2θ) | I/I$_o$ (%) |
| 9.66 | 2.4 | 15.45 | 2.3 | 15.06 | 6.9 |
| 10.27 | 1.6 | 15.92 | 15.9 | 15.71 | 22.3 |
| 10.47 | 2.2 | 16.67 | 1.7 | 15.87 | 7.4 |
| 10.91 | 6.3 | 16.98 | 3.1 | 16.35 | 34.5 |
| 13.63 | 2.1 | 18.28 | 17.8 | 16.77 | 12.3 |
| 14.09 | 4.6 | 18.56 | 7 | 17.28 | 10 |
| 15.10 | 4.1 | 20.58 | 13.1 | 17.62 | 47.9 |
| 15.52 | 10.5 | 20.85 | 8.8 | 18.09 | 43.9 |
| 16.45 | 9.1 | 21.64 | 3.9 | 20.43 | 42 |
| 16.67 | 7.6 | 22.19 | 4.8 | 20.80 | 33.6 |
| 17.21 | 4.9 | 22.65 | 2.9 | 21.31 | 42.7 |
| 17.53 | 2.4 | 23.28 | 3.4 | 21.71 | 13 |
| 18.33 | 28.2 | 23.97 | 11.8 | 21.85 | 14.5 |
| 18.69 | 11.1 | 24.31 | 6.3 | 22.13 | 12.8 |
| 19.37 | 3.5 | 25.52 | 3.9 | 22.26 | 16.3 |
| 20.29 | 8.6 | 26.20 | 3.4 | 23.51 | 13.2 |
| 20.64 | 17.2 | 26.47 | 3.1 | 23.69 | 15.9 |
| 21.02 | 12.7 | 28.84 | 6.4 | 23.91 | 25.6 |
| 21.68 | 5.1 | 30.13 | 3.5 | 24.31 | 38.7 |
| 22.01 | 8.3 | 31.12 | 2.9 | 25.22 | 8 |
| 22.29 | 8 | | | 25.67 | 8.9 |
| 23.17 | 7.8 | | | 27.05 | 18.9 |
| 23.39 | 9.1 | | | 27.89 | 13.3 |
| 24.30 | 13.6 | | | 28.24 | 8.6 |
| 25.76 | 3.4 | | | 28.71 | 21.3 |
| 26.05 | 4 | | | 29.89 | 8.9 |
| 26.63 | 5.5 | | | 30.24 | 18.7 |
| 27.01 | 3.1 | | | 30.88 | 5.8 |
| 27.49 | 2.8 | | | 31.44 | 7.6 |
| 28.10 | 1.8 | | | 33.06 | 4.5 |
| 28.73 | 10.9 | | | 34.36 | 6 |
| 29.42 | 3.2 | | | | |
| 30.00 | 3.7 | | | | |
| 30.89 | 2.1 | | | | |
| 31.34 | 2.4 | | | | |
| 31.70 | 1.1 | | | | |
| 32.81 | 1 | | | | |
| 32.91 | 0.8 | | | | |
| 33.48 | 2 | | | | |

Further Characterization of F-I, F-III, and F-V

Figure 5:
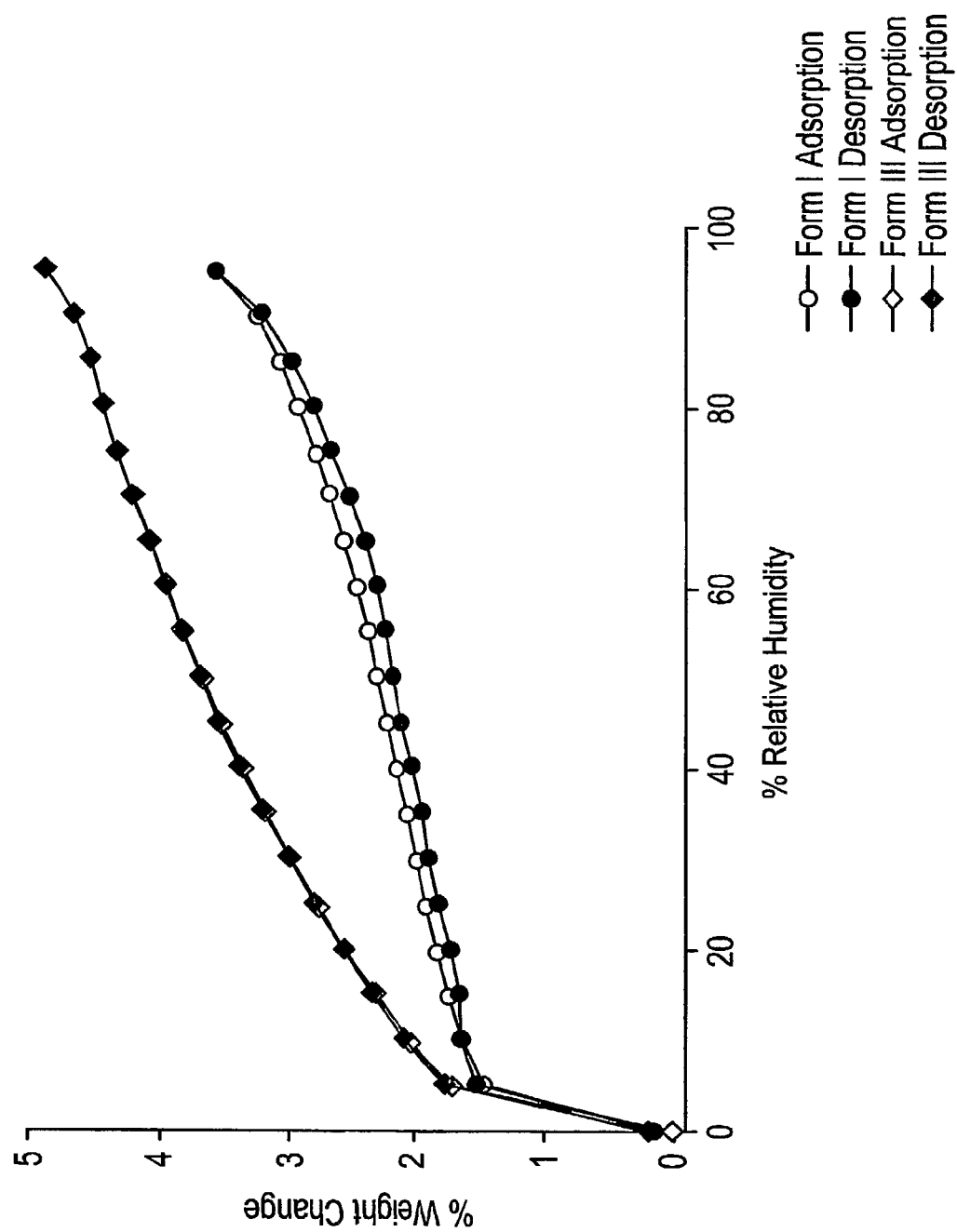
FIG. 5 depicts moisture sorption isotherms for F-I and F-III.

Hygroscopicity studies were performed on F-I and F-III. The moisture sorption isotherms for F-I and F-III are shown in FIG. 5. Upon initial exposure of the samples to approximately 5% R.H., there was an immediate weight gain of 1.5% and 1.7% moisture for F-I and F-III, respectively, equivalent to approximately 0.5 mole of water. Both forms show a continuous sorption of moisture through the entire humidity range, which is likely due to incorporation of water molecules in the lattices.

The difference in the moisture uptake of the two forms likely reflects the amount of water that can be incorporated into the two lattices (i.e., the amount of available space in the lattice that can accommodate water molecules). Lack of hysteresis in the sorption-desorption isotherms of F-I and F-III indicates that the crystal forms rapidly equilibrate at any given humidity.

The moisture sorption profiles for F-I and F-III reveal that these forms are essentially non-stoichiometric hydrates. At ambient relative humidities (about 50% R.H.), F-I contains about 2.2% water, slightly more than a true "hemihydrate" (1.7% theoretical), while F-III has sorbed sufficient moisture (about 3.7%) to be considered a "monohydrate" (3.4% theoretical). The bulk forms of F-I and F-III rapidly equilibrate with the atmosphere, so that the water content observed by analytical techniques is a reflection of the relative humidity at the time of data collection. Lot-to-lot differences observed in the DSC data likely results from the samples being hydrated to different extents due to different ambient storage conditions.

Figure 6:
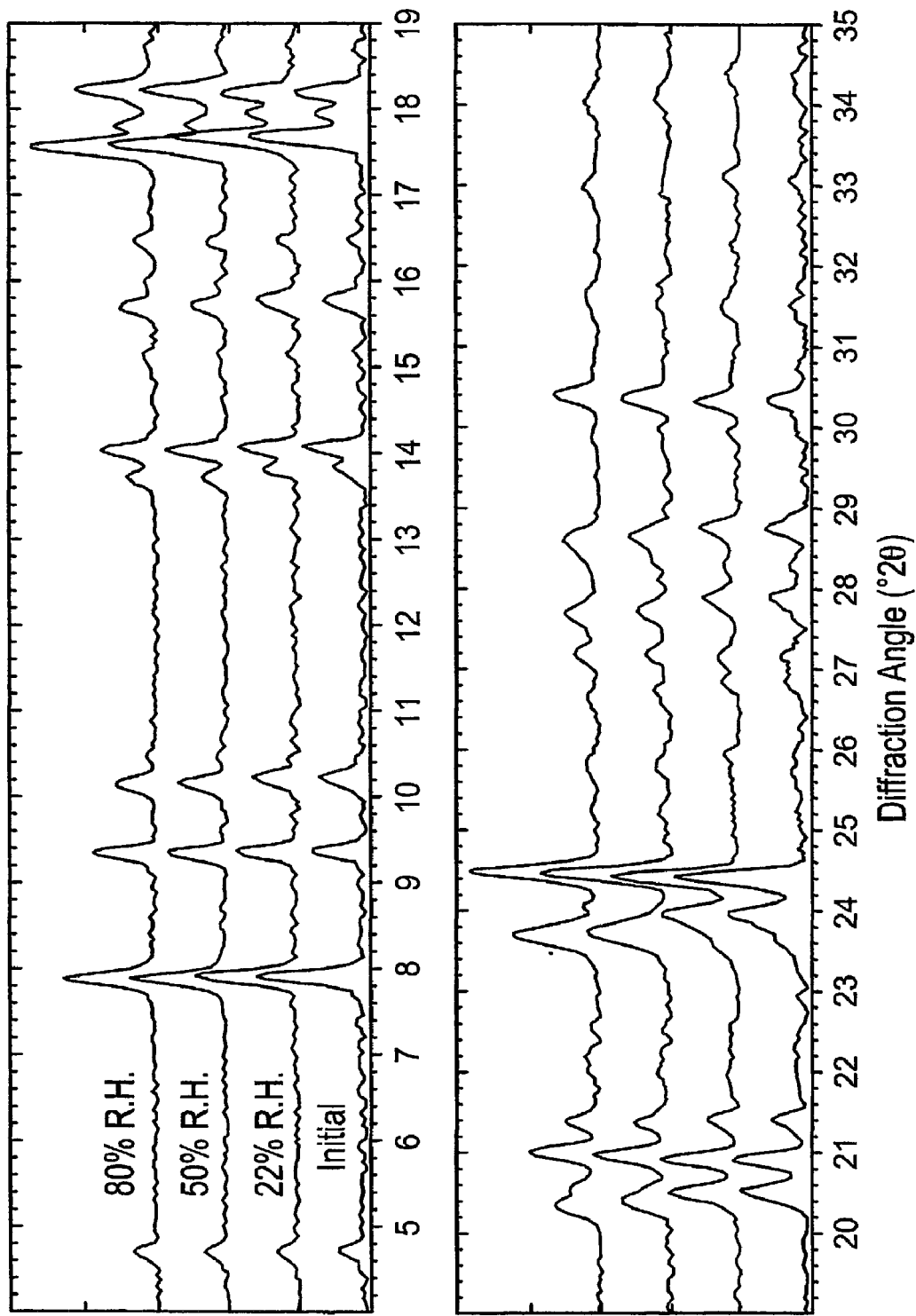
FIG. 6 depicts changes, as a function of relative humidity, in the XRD pattern for F-III.

XRD patterns were obtained for samples of F-I and F-III stored at different relative humidities. FIG. 6 depicts the changes observed when F-III was equilibrated at approximately 0, 22, 50 and 80% relative humidities (R.H.). There is a gradual shifting of the initial (0% R.H.) F-III peaks at about 13.8, 17.6, 18.0, 20.5 and 24.0° in 2θ as well as slight shifting of less intense peaks, as the relative humidity is increased. The observed changes in the XRD patterns of F-III indicate that the unit cell dimensions are changing, presumably to accommodate weakly held water molecules as the relative humidity is increased. The continuous shifting of peaks with humidity correlates well with moisture sorption data that showed a gradual weight gain over this R.H. range, providing evidence for variable hydrate formation.

Figure 7:
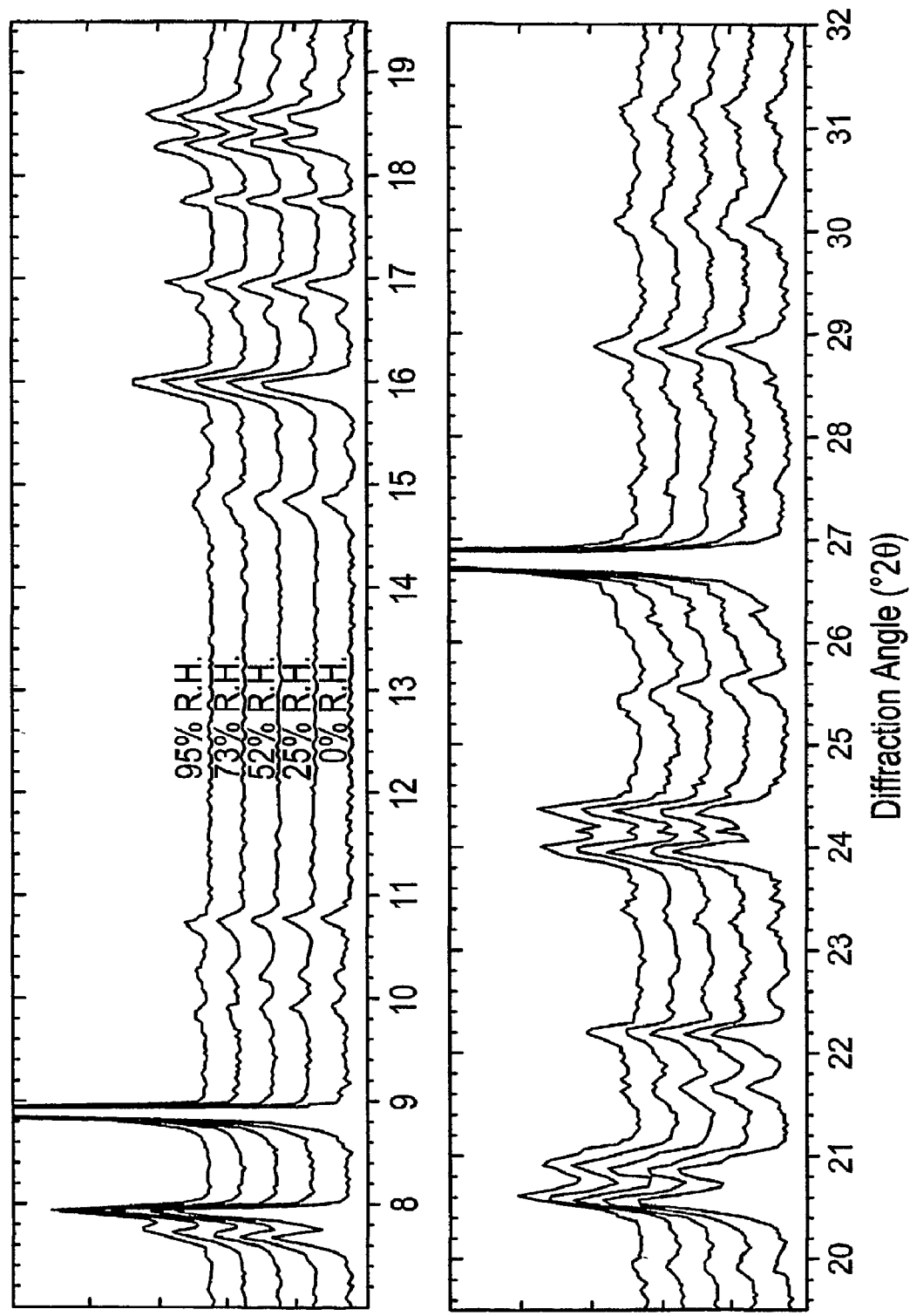
FIG. 7 depicts changes, as a function of relative humidity, in the XRD pattern for F-I.

A similar experiment was carried out on F-I to determine whether varying the relative humidity would have a similar effect on its lattice. FIG. 7 shows XRD patterns for samples of F-I that were equilibrated at approximately 0, 25, 52, 73 and 95% R.H. Intense reflections at about 8.8 and 26.8° in 2θ represent internal standard. Very slight shifting of the 0% R.H. peaks at about 7.7, 18.3, 18.5, 20.5, 20.8° in 2θ is observed as the relative humidity is increased. The peaks at about 7.7, 20.8, and 24.1 also appear to become slightly broadened and less resolved at higher relative humidities, indicating that water is being sorbed into amorphous components (or plasticizes the solid), particularly at 73 and 95% R.H. (see FIG. 5). The shifting of peaks in the XRD patterns of F-I is less dramatic than the peak shifts observed as F-III was exposed to different relative humidities. This suggests that the F-I lattice does not undergo the same expansion and/or contraction as the F-III lattice.

F-I and F-III were found to be physically stable over the entire relative humidity range, despite the ability of form III to sorb nearly twice as much water. The two forms were found to have comparable crystal size, morphology, aqueous solubilities and dissolution rates.

Figure 8:
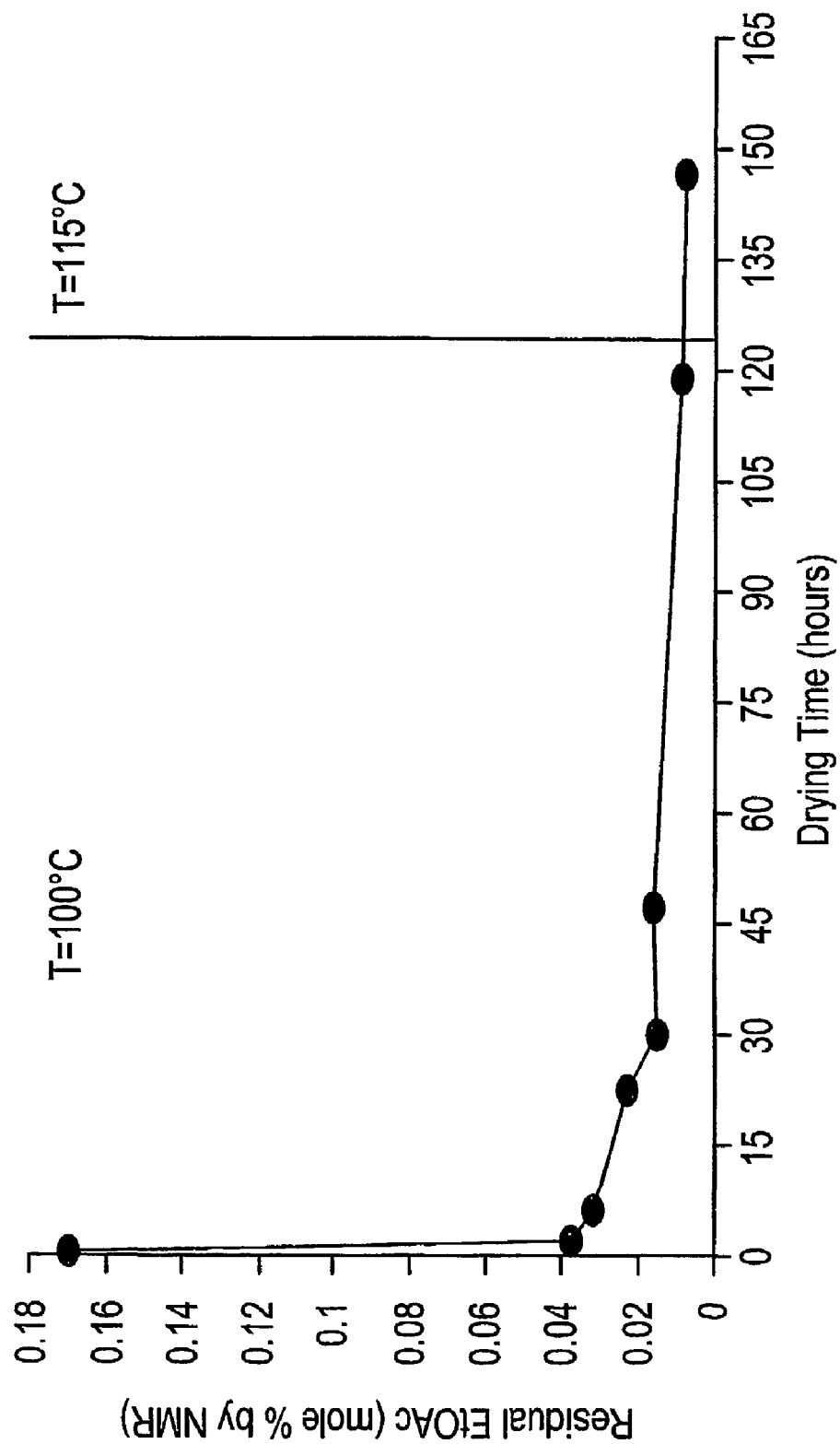
FIG. 8 depicts desolvation of S-II as a function of drying time and temperature.
Figure 9:
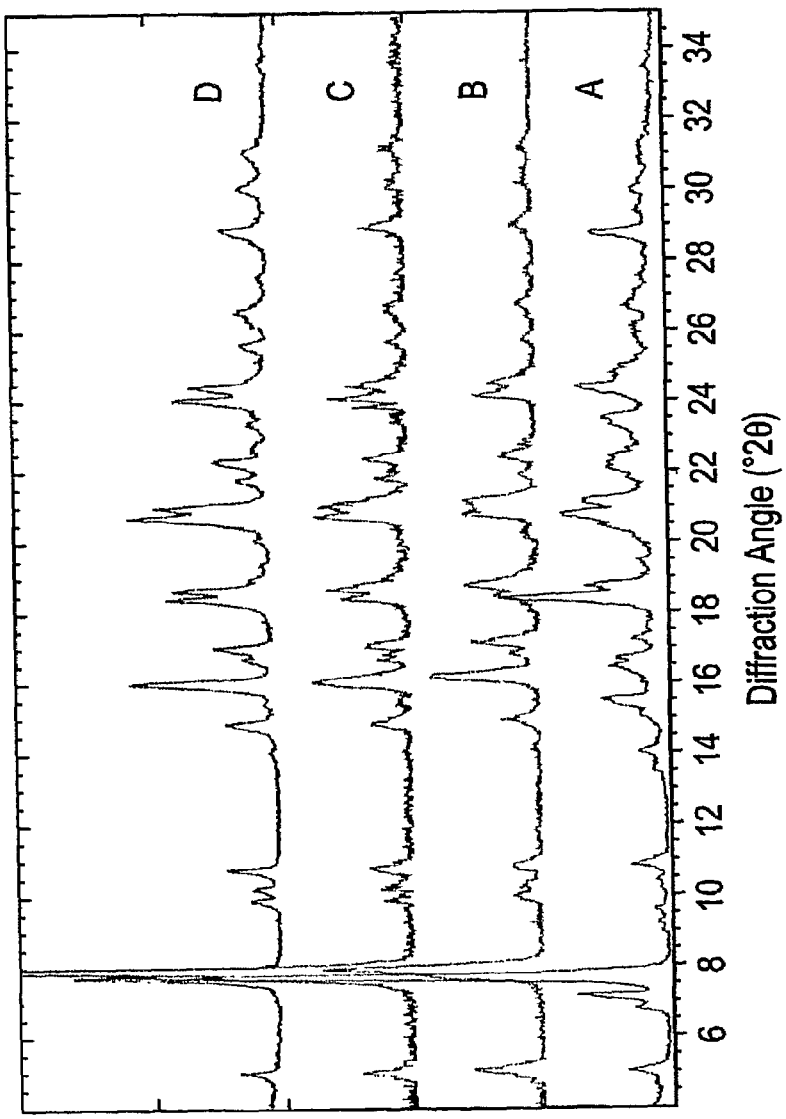
FIG. 9 depicts XRD patterns for selected time-points in the desolvation of S-II.

A drying study was carried out to monitor the desolvation of S-II as a function of drying time and temperature (see FIG. 8). XRD patterns for selected time-points are shown in FIG. 9. The XRD patterns demonstrate the changes that occur as the level of ethyl acetate in the crystal lattice decreases. The sample used in the drying study may have been partially desolvated because vacuum filtration was used to isolate the solid.

Many diffraction peaks from the desolvation study of S-II appear at similar angles, confirming that the lattices of S-II and F-I are very similar. The disappearance of diffraction peaks at about 6.8, 7.2 and 14.0° in 2θ after only minimal drying (time point B) suggests that these reflections may be attributed to crystallographic planes containing partial electron density of ethyl acetate molecules.

Extended annealing of the solvated material under vacuum at high temperatures yielded F-I. F-I prepared this way showed a high degree of crystallinity by XRD. Therefore, material generated by crystallization from a solution of ethanol and ethyl acetate followed by vacuum drying for only a few hours as taught in '474 showed very poor crystallinity because such a procedure results in partially desolvated S-II.

Figure 10:
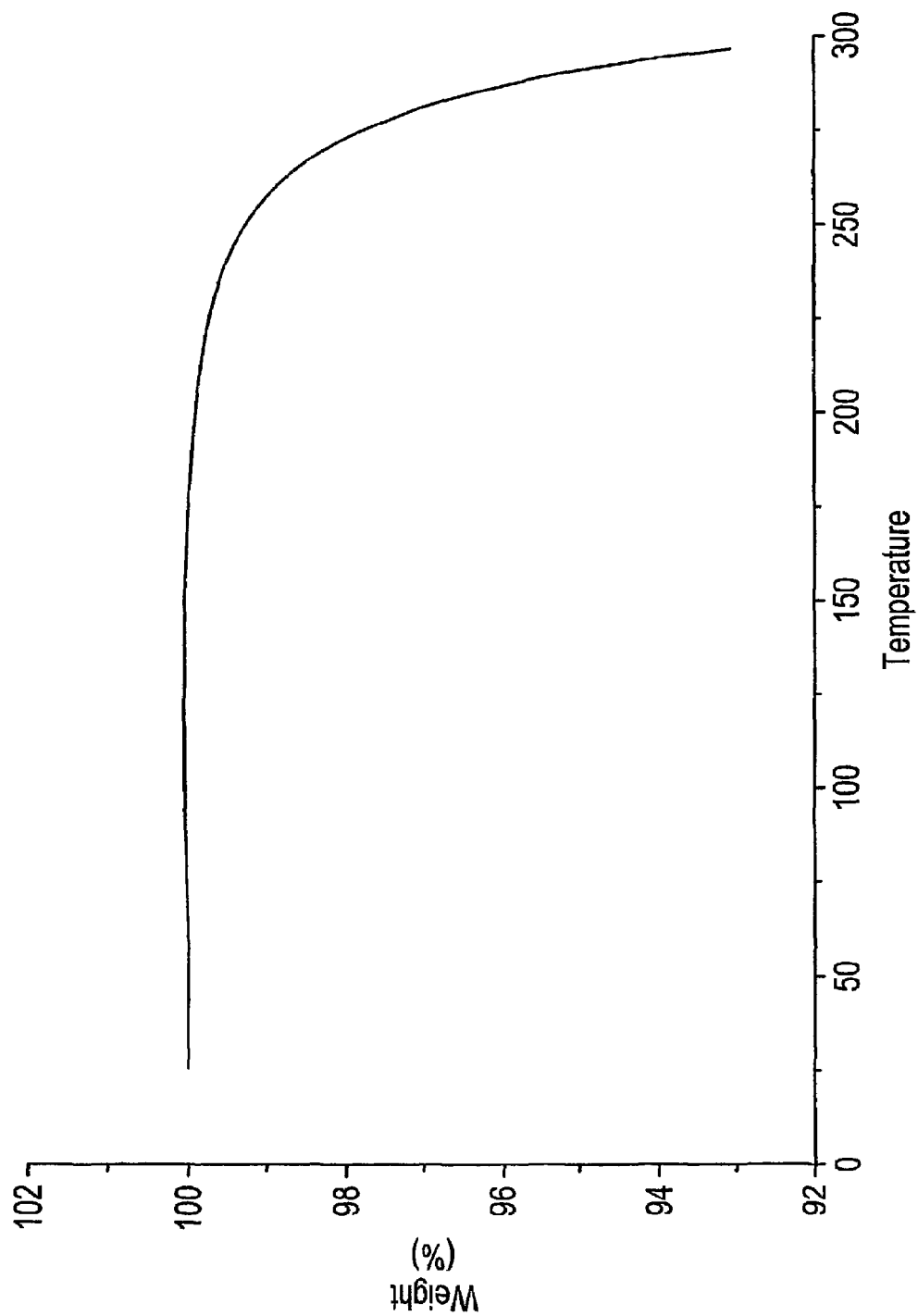
FIG. 10 is a representative TGA trace of F-V.
Figure 11:
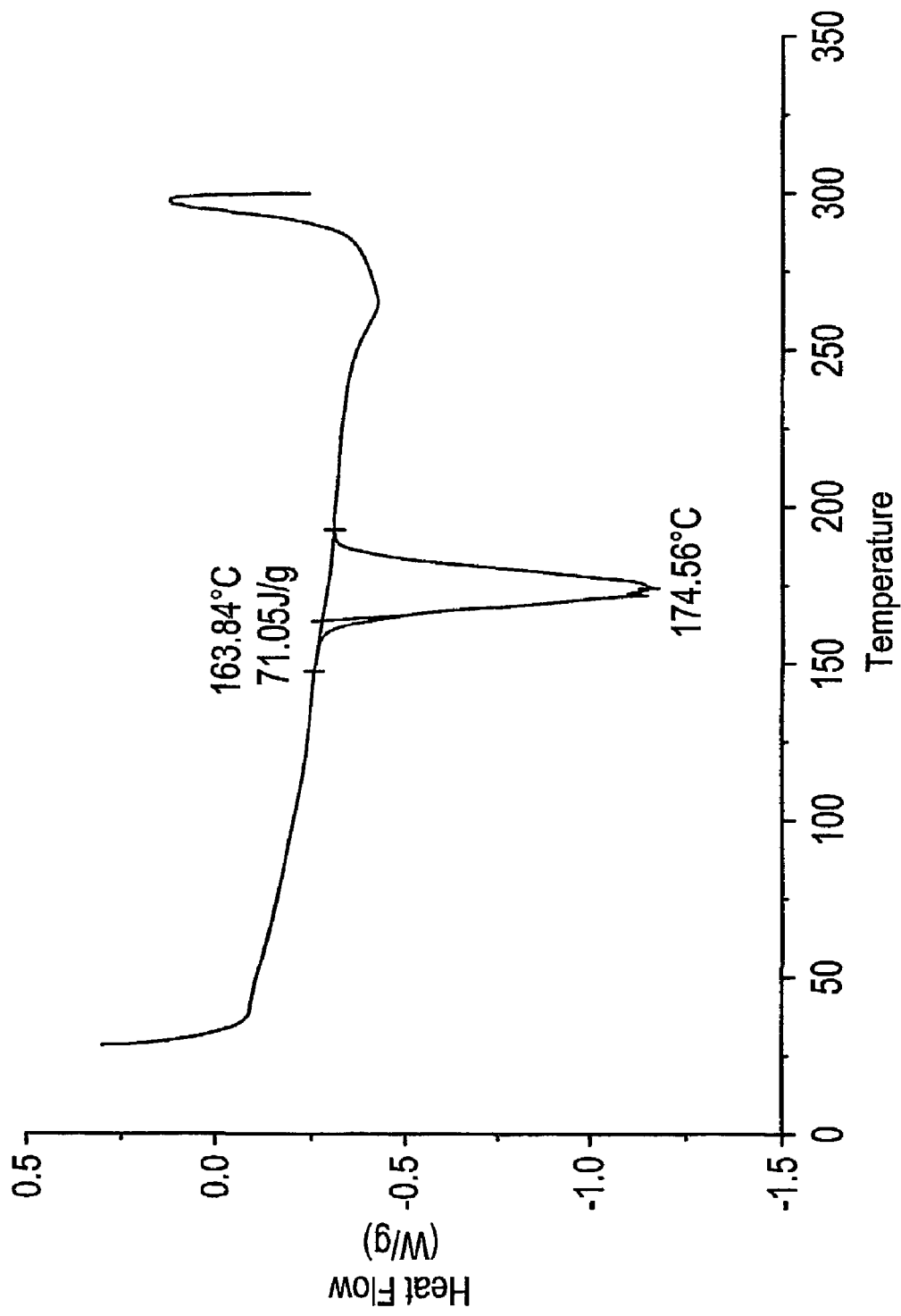
FIG. 11 is a representative DSC trace of F-V.

A representative TGA trace of F-V is shown in FIG. 10. Thermogravimetric analysis of F-V showed no weight loss indicating the isolation of a non-solvated crystal form. DSC analysis of F-V showed a sharp melting endotherm at 174–175° C. as shown in FIG. 11, which is significantly higher than that observed for F-III.

The moisture sorption/desorption isotherm obtained for F-V showed a weight increase of 0.11% over the range of 0–95% RH indicating a stable anhydrous crystal form with little propensity to adsorb water or convert to a hydrated form of arzoxifene hydrochloride.

The XRD pattern of F-V features sharp peaks and a flat baseline, indicative of highly crystalline materials. The angular peak positions in 2θ and corresponding $I/I_o$ data for all peaks with intensities equal to or greater than 10% of the largest peak for F-V is tabulated in Table 1A. All data in Table 1A are expressed with an accuracy of ±0.22°. Although many of the intense reflections are generally at similar diffraction angles to those reported for S-II, F-I and F-III, each of the forms gives a different powder pattern, allowing for a clear distinction between S-II, F-I, F-III and F-V.

Variable temperature x-ray powder diffraction analysis of F-V showed no significant change in the diffraction pattern up to 125° C. which is consistent with the DSC profile indicating a stable crystal form.

TABLE 1A

| Angle 2θ | $I/I_o$ (%) | Angle 2θ | $I/I_o$ (%) | Angle 2θ | $I/I_o$ (%) |
|---|---|---|---|---|---|
| 7.3 | 45 | 17.6 | 72 | 22.6 | 19 |
| 9.0 | 22 | 17.9 | 83 | 23.3 | 20 |
| 10.0 | 10 | 18.2 | 56 | 24.4 | 46 |
| 12.8 | 39 | 18.9 | 82 | 25.8 | 38 |
| 14.6 | 15 | 19.8 | 27 | 27.4 | 32 |
| 15.5 | 50 | 21.5 | 100 | 28.2 | 18 |
| 15.9 | 64 | | | | |

F-I and F-III have several advantages over the prior art form of arzoxifene hydrochloride described above. Relative to the arzoxifene hydrochloride produced by the procedures taught in '474, F-I and F-III are more physically stable at ambient temperature and are, therefore, more amenable to pharmaceutical development, i.e., development of a dosage formulation. In addition, F-I and F-III are much more crystalline than the form disclosed in '474. Crystalline materials are generally less hygroscopic and more stable (i.e., less prone to chemical degradation) than amorphous materials and are, therefore, more desirable for formulation processing. Furthermore, unlike the form of arzoxifene hydrochloride produced by the procedures taught in '474, which contained ethyl acetate and water in its lattice, F-I and F-III contain only water.

F-V has several advantages over the prior art form of arzoxifene hydrochloride described in '474 and over F-I and F-III described in the previously incorporated by reference PCT applications. Relative to the arzoxifene hydrochloride produced by the procedures taught in '474, F-V is more stable at ambient temperature and is, therefore, more amenable to pharmaceutical development, i.e., development of a dosage formulation. In addition, unlike the form disclosed in '474, F-V is highly crystalline. Crystalline materials are generally less hygroscopic and more stable (e.g., less prone to chemical degradation, maintains consistent potency) than amorphous materials and are, therefore, more desirable for formulation processing. Furthermore, unlike the form of arzoxifene hydrochloride produced by the procedures taught in '474, which contained ethyl acetate and water in its lattice, F-V contains neither.

Unlike S-II, F-I and F-III, F-V is truly an anhydrous form of arzoxifene hydrochloride which shows no propensity to adsorb water on changes in relative humidity. Furthermore, F-V's crystal lattice is stable up to its melting temperature. Moreover, F-V has approximately a 10% higher aqueous solubility relative to F-III and is the thermodynamically most stable known form of arzoxifene hydrochloride at ambient storage conditions.

Characterization Methods for S-II, F-I and F-III

DSC measurements were performed on a TA Instruments 2920 Modulated DSC attached to a Thermal Analyst 3100 and equipped with a refrigerated cooling system. Samples (3–5 mg) were heated in crimped aluminum pans from 10 to 240° C. at a heating rate of 2° C./min.

TGA analyses were performed on a TA Instruments 2050 Thermogravimetric Analyzer attached to a Thermal Analyst 3100. Samples (5–10 mg) were heated in open pans from 25° C. to 250° C. at a heating rate of 5° C./min.

XRD patterns were obtained on a Siemens D5000 X-ray powder diffractometer, equipped with a CuKα source (λ=1.54056 Å) and a Kevex solid-state detector, operating at 50 kV and 40 mA. Each sample was scanned between 4° and 35° in 2θ. Samples were allowed to equilibrate for at least 30 minutes at the desired temperature and/or relative humidity before data collection.

Hygroscopicity measurements were made for F-I and F-III using the VTI method as follows. Each sample was dried under vacuum at 60° C. until no further weight loss was detected, at which time the sample chamber was brought to 0% relative humidity. Moisture sorption isotherms were obtained at 25° C. using a VTI vacuum moisture balance with the following conditions: sample size 10–15 mg, adsorption/desorption range 0–95% relative humidity, step interval 5%, sample interval 10 minutes.

Characterization Methods for F-V

DSC analysis was performed using a TA Instruments 2920 equipped with an auto-sampler and a refrigerated cooling device. The sample was enclosed in a crimped aluminum pan and analyzed vs. an empty reference pan. The heat flow was measured after equilibration at 30° C. The heating rate was 5° C. per minute to 300° C. A graph of heat flow vs. temperature was integrated to identify any endothermic or exothermic events.

TGA analysis was performed using a TA Instruments 2950 equipped with an auto-sampler. The sample was loaded onto a tared aluminum pan and the temperature was ramped from ambient to 300° C. at a rate of 10° C. per minute. A graph of weight percent vs. temperature was integrated to determine the percent loss.

Moisture Sorption Isotherms were generated using a VTI SGA-100 flow instrument. The samples were analyzed at 25° C. from 0–95% relative humidity (RH) for adsorption and from 95–5% RH for desorption in steps of 5% RH. The adsorption and desorption isotherms were generated as a graph of the % weight change vs. % RH.

X-ray powder diffraction patterns were obtained on a Siemens D5000 X-ray powder diffractometer which was equipped with a CuKα source (λ=1.54056 Å) operated at 50 kV and 40 mA with a Kevex solid state Si(Li) detector. The samples were scanned from 4 to 35° in 2θ at 2.5 seconds per step size of 0.04°. The dry powders were packed into recessed top-loading sample holders and a smooth surface was obtained using a glass slide.

Variable temperature X-ray powder diffraction patterns were obtained on a Siemens D5000 X-ray powder diffractometer which was equipped with a CuKα source (λ=1.54056 Å) operated at 50 kV and 40 mA with a scintillation detector and nickel filter. The powder was packed into a top-loading, recessed temperature controlled holder and a smooth surface was obtained for diffraction. The sample was scanned from 2 to 35° 2θ at 2.5 seconds per step size of 0.04° beginning at 25° C. after an equilibration time of 5 minutes. Subsequent scans were obtained at increasing temperature increments of 25° C. to a maximum of 125° C.

The following preparative examples further illustrate processes for preparing the crystalline forms of arzoxifene hydrochloride used in the pharmaceutical formulations of the present invention. The examples are not intended to be limiting to the scope of these formulations in any respect, and should not be so construed.

Preparation 1

F-III From 6-Isopropoxy-3-(4-[2-(piperidin-1-yl)ethoxy]phenoxy)-2-(4-methoxyphenyl)benzo[b]thiophene Hydrochloride To a methylene chloride solution (100 mL) of 6-isopropoxy-3-(4-[2-(piperidin-1-yl)ethoxy]phenoxy)-2-(4-methoxyphenyl)benzo[b]thiophene hydrochloride (10 g, 18 mmol) under a nitrogen atmosphere at −10° C. to −20° C., was added $BCl_{3(g)}$ (4.23 g, 34 mmol) at a rate which maintains the temperature of the reaction below −10° C. After the addition was complete, the reaction was allowed to stir for an additional 2 hours. To the reaction, isopropyl alcohol (IPA, 12.35 mL, 167 mmol) was slowly added at less than −10° C. and stirring was continued for 30 minutes. A separate flask was charged with 100 mL water and cooled with an ice bath to approximately 0° C. The product solution was transferred to the water via cannula, maintaining vigorous stirring. The resultant white slurry was allowed to stir at 0° C. for 1 hour. The product was recovered by filtration and rinsed with 25 mL 40% $CH_2Cl_2$/water then with 25 mL cold water. The product was suspended into 60 mL IPA and 60 mL water and heated to 60° C. A solution was obtained at 48° C. Additional water (120 mL) was added. The solution was allowed to cool to 35° C. and the slurry was further cooled slowly to 0–5° C. and stirred for several hours. The product was isolated by filtration and washed with cold deionized water (25 mL). F-III wetcake was dried to a constant weight in vacuo at 50° C. for 12 to 24 hours to provide F-III.

Preparation 2

F-III From 6-Benzyloxy-3-(4-[2-(piperidin-1-yl)ethoxy]phenoxy)-2-(4-methoxyphenyl)benzo[b]thiophene-(S-oxide)

To a 250 mL Parr bottle was added deionized water (5.25 mL), 1M HCl (7.74 mL, 7.75 mmol), 10% Pd/C (type A32110, 1.37 g, 1.29 mmol Pd), [6-benzyloxy-3-(4-[2-(piperidin-1-yl)ethoxy]phenoxy)-2-(4-methoxyphenyl)benzo[b]thiophene-(S-oxide) (3 g, 5.16 mmol), and isopropyl alcohol (32 mL) at ambient temperature. The bottle was fitted to a Parr shaker, sequentially evacuated and gassed with nitrogen twice, and subsequently evacuated and filled with hydrogen gas to a pressure of 30 psig. The shaker was started and the reaction mixture was heated to 60° C. The reaction was determined to be complete by HPLC analysis after approximately 4 hours. The reaction mixture was filtered through a pad of diatomaceous earth, and the pad was washed with 0.1 M HCl (2×10 mL). The solvent was removed in vacuo at approximately 50° C. The resultant residue was dissolved into 50% isopropyl alcohol/deionized water (30 mL) and gently heated on a steam bath until a solution was obtained. To the solution was added deionized water (22 mL) and the solution was allowed to cool to ambient temperature. The product slurry is further cooled to 0° C. The product was isolated by filtration, washed with cold deionized water (2×15 mL)), and dried in vacuo at 50° C. to constant weight to provide F-III.

Preparation 3

F-I from S-II

S-II was dried in a vacuum oven (−25 in. Hg) at 100° C. for 118 hours to yield F-I.

Preparation 4

F-V: Crystallization from Methanol without Concentration

A 20.00 g sample of arzoxifene hydrochloride is combined with 500 ml of anhydrous methanol (HPLC grade) and heated to reflux. All of the solids dissolve to afford a homogeneous pale yellow solution. The solution is cooled to below reflux and 5.00 g of additional arzoxifene hydrochloride are added. The solution is re-heated to reflux to effect dissolution of all of the solids. The solution is slowly allowed to cool with agitation. At 50° C. the solution is seeded with several milligrams of previously prepared F-V salt. The crystalline slurry is allowed to cool from 50° C. to 30° C. over a 1.25 hour period. At this point a large amount of white solids is present. The stirred slurry is immersed in an ice bath and stirred for an additional 3 hours. The slurry is filtered using Whatman #1 filter paper and the white solid is washed with 50 ml of methanol pre-chilled to 0° C. The wet cake is dried for about 48 hours at 50° C. under vacuum with a slight $N_2$ purge. Yield 15.94 g (63.8% yield). HPLC potency 89.4% (as free base), total related substances (TRS) 0.28%. Comparison of the product weight before and after drying showed the initial wet cake contained 65% solvent.

Preparation 5

F-V: Crystallization from Methanol with Concentration

A 25.00 g sample of arzoxifene hydrochloride is combined with 500 ml of anhydrous methanol (HPLC grade) and heated to reflux. All of the solids dissolved to afford a homogeneous pale yellow solution. The solution is concentrated by removal of 375 ml of distillate by atmospheric distillation. At this point, the reaction mixture is a clear homogeneous yellow solution. Reflux is broken and the solution is seeded with several milligrams of previously prepared F-V. After seeding, the mixture is allowed to cool to ambient temperature with slow agitation over a 1 hour period. During this time a large amount of white precipitate forms. The slurry is immersed in an ice bath and stirred for an additional 3 hours. The slurry is filtered using Whatman #1 filter paper and the white solid is washed with 50 ml of methanol pre-chilled to 0° C. The wet cake is dried for about 48 hours at 50° C. under vacuum with a slight $N_2$ purge. Yield 22.44 g (89.8% yield). HPLC potency 91.3% (as free base), TRS 0.26%. Comparison of the product weight before and after drying showed the initial wet cake contained 31.5% solvent.

Preparation 6

F-V: 30 Gallon Scale Recrystallization from Methanol

A 3.08 kg sample of arzoxifene hydrochloride is combined with 60 L of anhydrous methanol (HPLC grade) and heated to reflux. All of the solids dissolved to afford a pale yellow homogeneous solution. The solution is concentrated by removal of 40 L of distillate by atmospheric distillation. At this point, the reaction mixture is a clear homogeneous yellow solution. The reaction is cooled to break reflux and the manway is opened at about 40° C. to check for crystallization. Crystals are observed and cooling is continued at a rate 12° C. per hour to a final temperature of 0° C. The crystallization slurry is stirred overnight at 0° C. and then filtered through a single plate filter press. In order to remove all product from the crystallization tank, the mother liquor is used as a tank wash and then sent through the press. The wet cake is then washed with 11.3 L of anhydrous methanol pre-chilled to 0° C. The wet cake is dried by applying vacuum to the press and running 50° C. water through the jacket of the press. A slight $N_2$ purge is applied after about 24 hours. Total drying time is about 36 hours. The yield is 2.588 kg (86.27%); HPLC potency 92.7 (as free base); TRS 0.39%.

Preparation 7

F-V: Crystallization from Ethanol

Figure 12:
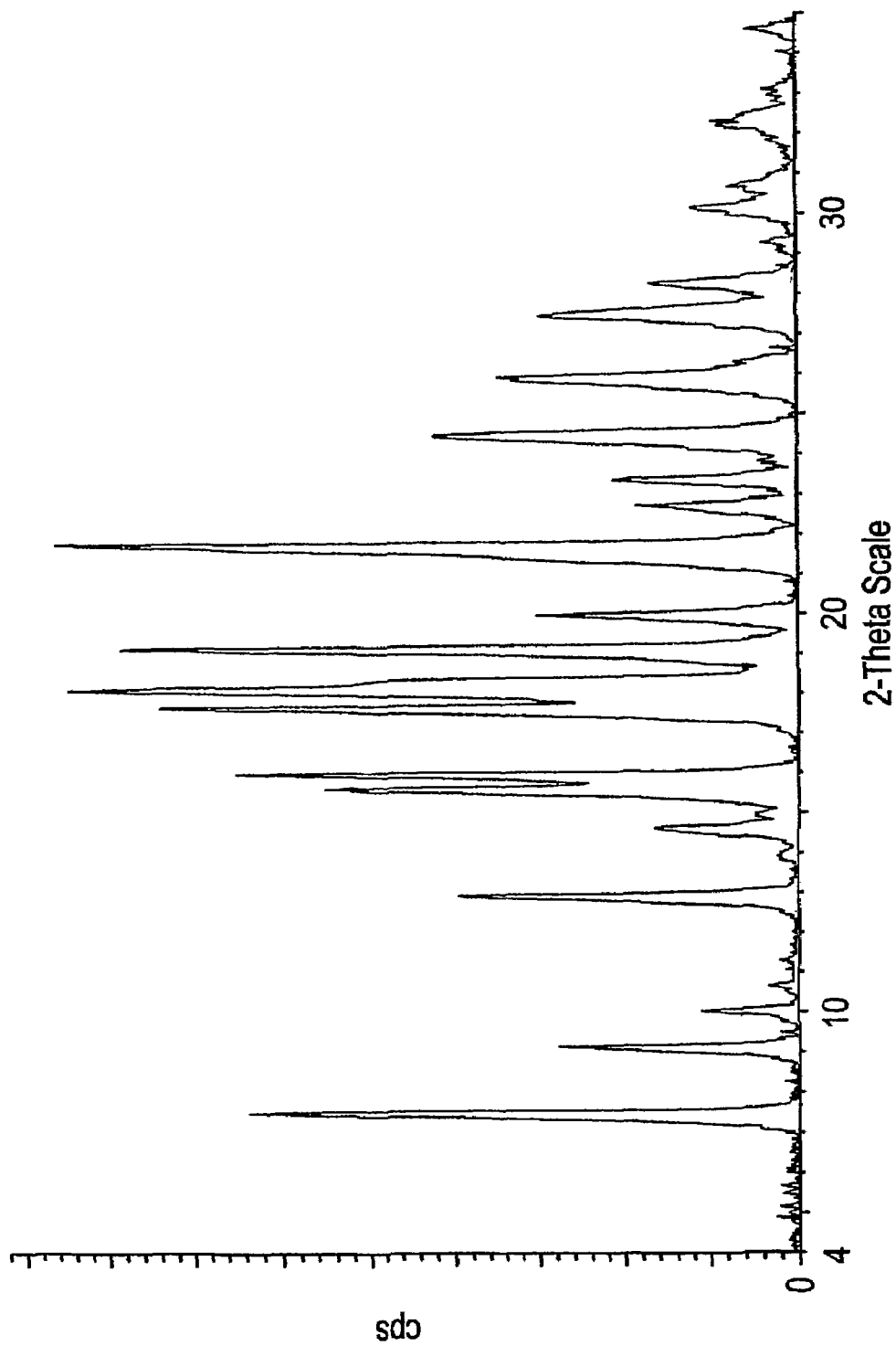
FIG. 12 is a representative XRD pattern for F-V.

Punctilious ethanol (250 ml) and arzoxifene hydrochloride (10.0 g) were combined and heated to reflux to effect dissolution. The solution was allowed to cool to ambient temperature over a 3 hour period during which time a white crystalline precipitate formed. The solids were isolated by filtration and vacuum dried overnight at 50° C. with a slight $N_2$ purge. Yield 5.50 g, m.p. 173° C. (by DSC). An x-ray powder diffraction spectrum for this sample was obtained and was substantially identical to that of the F-V pattern disclosed in FIG. 12.

Preparation 8

F-V: Crystallization from Isopropanol

Anhydrous isopropanol (250 ml) and arzoxifene hydrochloride (10.0 g) were combined and heated to reflux to effect dissolution. Heat was removed and the solution seeded with several milligrams of F-V. The reaction mixture was allowed to cool to ambient temperature and stir overnight during which time a white precipitate formed. The solids were isolated by filtration to afford 12.11 g of wetcake. A 4.01 g sample of the wetcake was dried over night at 60° C. under vacuum with a slight $N_2$ purge. Yield 2.72 g; m.p. 171.5° C. (by DSC). An x-ray powder diffraction spectrum for this sample was obtained and was substantially identical to that of the F-V pattern disclosed in FIG. 12.

Preparation 9

F-V: Preparation from Arzoxifene Free Base

Arzoxifene free base (5.07 g) was slurried in 65.0 ml of methanol. A solution of 1.41 ml of concentrated hydrochloric acid and 10.0 ml of water was added to the reaction mixture. The reaction mixture was heated to 55° C. for 15 minutes to effect dissolution. The reaction mixture was cooled to 30° C. and seeded with 50 mg of F-V. The reaction mixture was cooled to 10° C. at a rate of 1° C./hr and stirred at that temperature for 8 hours. The solids were isolated by filtration, washed with methanol pre-chilled to 10° C. and vacuum dried at 50° C. over night with a light $N_2$ purge. Yield 4.42 g (87.7% yield); potency (HPLC) 99.7%; TRS 0.32%. An x-ray powder diffraction spectrum for this sample was obtained and was substantially identical to that of the F-V pattern disclosed in FIG. 12.

The term "salt" as used in the claims refers generally to "pharmaceutically acceptable salt" and represents salt forms of 6-hydroxy-3-(4-[2-(piperidin-1-yl)ethoxy]phenoxy)-2-(4-methoxyphenyl)benzo[b]thiophene and the named stabilizing agents that are physiologically suitable for pharmaceutical use. The pharmaceutically acceptable salts can exist in conjunction with 6-hydroxy-3-(4-[2-(piperidin-1-yl)ethoxy]phenoxy)-2-(4-methoxyphenyl)benzo[b]thiophene as addition primary, secondary, tertiary or quaternary ammonium, alkali metal or alkaline earth metal salts. Generally, the acid addition salts are prepared by the reaction of an acid with 6-hydroxy-3-(4-[2-(piperidin-1-yl)ethoxy]phenoxy)-2-(4-methoxyphenyl)benzo[b]thiophene. The alkali metal and alkaline earth metal salts are generally prepared by the reaction of the metal hydroxide of the desired metal salt with 6-hydroxy-3-(4-[2-(piperidin-1-yl)ethoxy]phenoxy)-2-(4-methoxyphenyl)benzo[b]thiophene.

The term "pharmaceutical" when used herein as an adjective, means substantially non-toxic and substantially non-deleterious to the recipient.

By "pharmaceutical formulation" it is further meant that the combination of solvents, excipients, and salt must be compatible with the active ingredient of the formulation.

The term "acid addition salt" refers to a salt of 6-hydroxy-3-(4-[2-(piperidin-1-yl)ethoxy]phenoxy)-2-(4-methoxyphenyl)benzo[b]thiophene or the cysteine, acetylcysteine or methionine stabilizing agents prepared by reaction of said compound with a mineral or organic acid. For exemplification of pharmaceutical acid addition salts see, e.g., Berge, S. M, Bighley, L. D., and Monkhouse, D. C., *J. Pharm. Sci.*, 66:1, 1977. Acids commonly employed to form such acid addition salts include inorganic acids such as hydrochloric, hydrobromic, hydroiodic, sulfuric, and phosphoric acid, as well as organic acids such as toluenesulfonic, methanesulfonic, oxalic, para-bromophenylsulfonic, carbonic, succinic, citric, benzoic, and acetic acid, and related inorganic and organic acids. Such pharmaceutically acceptable salts thus include sulfate, pyrosulfate, bisulfate, sulfite, bisulfite, phosphate, meta-phosphate, pyrophosphate, chloride, bromide, iodide, acetate, propionate, decanoate, caprolate, acrylate, formate, isobutyrate, caprate, heptanoate, oxalate, malonate, succinate, subarate, sebacate, fumarate, hippurate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, α-hydroxybutyrate, glycolate, tartrate, methanesulfonate, propanesulfonate, naphthalene-1-sulfonate, napthalene-2-sulfonate, mandelate, and the like salts.

The term "Arzoxifene N-Oxide Degradation Product" refers to a compound of the formula:

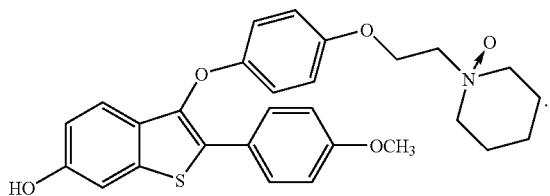

The term "Arzoxifene Cleavage Degradation Product" refers to a compound of the formula:

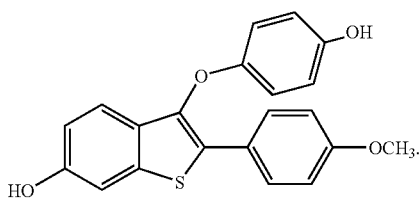

It has been found that pharmaceutical formulations of 6-hydroxy-3-(4-[2-(piperidin-1-yl)ethoxy]phenoxy)-2-(4-methoxyphenyl)benzo[b]thiophene or a salt thereof may be stabilized to decomposition during the manufacturing process or during storage by the addition to said formulation a stabilizing agent selected from methionine, acetylcysteine, cysteine or salts thereof. These compounds are commercially available amino acids or amino acid derivatives, each of which can exist as the racemate or pure D- or L-forms. Preferably the stabilizing agent is cysteine hydrochloride; most preferably L-cysteine hydrochloride monohydrate.

For purposes of the present invention, one or more (preferably one) of the stabilizing agents disclosed herein is present in the pharmaceutical formulation in an amount sufficient to effect stabilization to decomposition of the formulation. The amount of stabilizer may vary from about 0.01 to about 10 percent by weight of the total composition and is preferably from about 0.05 to about 5 percent weight of the total composition. Generally, the amount of these stabilizing agents will be about 0.01 to about 1.00 times the amount of active ingredient in the formulation. The precise amount of stabilizing agent used in a particular formulation will, of course, vary depending upon the ultimate size of the dosage form, the specific dosage form chosen, the amount of active ingredient present in the dosage form, the quantitative level of excipients, and the like. Suffice it to say that the pharmaceutical formulation will contain the stabilizing agent in an amount sufficient to effect stabilization to degradation of said formulation. That is, the formulation will be less readily decomposed when one of the stabilizing agents disclosed herein is incorporated with said formulation. The amount of stabilizing agent sufficient to effect stabilization can be readily determined by one of ordinary skill in the art according to well established routine test methods. In particular, whether or not an amount of the stabilizer is effective can be ascertained by testing the formulation against a formulations lacking a stabilizer as set out in the Examples below.

The stabilized pharmaceutical formulations as disclosed herein contain a therapeutically effective amount of 6-hydroxy-3-(4-[2-(piperidin-1-yl)ethoxy]phenoxy)-2-(4-methoxyphenyl)benzo[b]thiophene or a salt thereof. As used herein, the term "therapeutically effective" refers to that amount of active ingredient or salt thereof sufficient to deliver, in single or divided doses, from about 1 to 100 mg of active ingredient per day to the subject being administered. In a preferred embodiment, when 6-hydroxy-3-(4-[2-(piperidin-1-yl)ethoxy]phenoxy)-2-(4-methoxyphenyl)benzo[b]thiophene hydrochloride is the active ingredient in the formulation, it is present in an amount sufficient to deliver in single or divided doses, 0.1 to 100 mg of active ingredient per day to the subject being administered. Preferably, the active ingredient is present in an amount of about 1 mg to about 40 mg; or from about 5 mg to about 30 mg. Most preferably, approximately 21.53 mg of a salt of 6-hydroxy-3-(4-[2-(piperidin-1-yl)ethoxy]phenoxy)-2-(4-methoxyphenyl)benzo[b]thiophene, especially the hydrochloride salt, which is equivalent to approximately 20 mg of the free base, is administered in single or divided doses to a patient at about 20 mg per day. The skilled artisan will readily recognize that the therapeutically effective amount may vary widely particularly where the route of administration and the particular salt or free base being employed are considerations. Of course, other factors such as the weight or age of the subject being treated as well as the time, frequency and specific pharmaceutical formulation employed in the administration are to be considered in determining the therapeutically effective amount in a given situation. This amount may be readily ascertained in a particular instance by the skilled artisan utilizing conventional dose titration techniques.

The pharmaceutical formulations of 6-hydroxy-3-(4-[2-(piperidin-1-yl)ethoxy]phenoxy)-2-(4-methoxyphenyl)-benzo[b]thiophene or a salt thereof stabilized to decomposition are preferably formulations for oral administration. Such formulations include any of the conventional solid or liquid dosage forms, such as, for example, tablets, capsules, powders, suspensions, and the like including any sustained release preparations thereof. In addition to 6-hydroxy-3-(4-[2-(piperidin-1-yl)ethoxy]phenoxy)-2-(4-methoxyphenyl)benzo[b]thiophene or a salt thereof and stabilizing agent, the pharmaceutical formulations of the present invention for oral administration utilize pharmaceutically acceptable excipients including, but not limited to diluents, binders, disintegrants, surfactants, lubricants, film coating polymers, and the like such as glucose, lactose (anhydrous lactose and lactose monohydrate), sucrose, dicalcium phosphate, corn and potato starch, microcrystalline cellulose, povidone, gelatin, hydroxpropylmethylcellulose, hydroxypropylcellulose, powdered gum tragacanth, methylcellulose, crospovidone, sodium starch glycolate, sodium carboxymethylcellulose, polysorbate 80, sodium lauryl sulfate, stearic acid, sodium, calcium and magnesium stearates among others; as well as various buffering agents, emulsifiers, dispersing agents, flavoring agents, colorants, plasticizers and the like.

Preparation of the pharmaceutical formulations disclosed herein are readily achieved by one skilled in the art. Further, the skilled artisan will appreciate that the ultimate pharmaceutical formulation may be provided in multiple or discrete, unit dose fashion with the latter being preferred. In addition to the information provided herein pertinent to the preparation of the pharmaceutical compositions of the invention, further reference may be obtained from standard treatises such as *Remington's Pharmaceutical Sciences*, Seventeenth Edition, Mack Publishing Co., Easton, Pa. (1985) which is incorporated herein by reference.

The invention will now be illustrated by the following examples which shall not be construed as a limitation thereon.

Examples of Cysteine Hydrochloride as a Stabilizer

A. 10 mg and 20 mg Arzoxifene Formulations

Core tablets weighing approximately 250 mg and containing approximately 10 mg or 20 mg of arzoxifene as arzoxifene hydrochloride were prepared generally as follows. The arzoxifene hydrochloride, water soluble diluents (lactose monohydrate and anhydrous lactose), and a portion of the distintegrant (crospovidone) were blended in a high shear granulator. This blend was then wet massed in the high shear granulator with an aqueous solution of povidone and polysorbate 80. In those formulations which contain the stabilizer (cysteine hydrochloride), the cysteine hydrochloride is also dissolved in the granulation solution and added during the wet mass step via the granulation solution. The cysteine hydrochloride is preferably added to the granulation solution after the addition of the povidone and polysorbate 80. To maintain a constant tablet fill weight, the amount of lactose (lactose monohydrate and anhydrous lactose) was reduced corresponding to the amount of cysteine hydrochloride added. Following a wet sizing step through a rotating impeller mill, the granules were dried using a fluid bed dryer. The dried granules were reduced to a suitable size with a rotating impeller mill. The remaining ingredients (microcrystalline cellulose, magnesium stearate, and rest of the crospovidone) were added to the dried granules and blended. This mixture was then compressed into round shaped tablets using a conventional rotary tablet press. For tablet lots A, B, and C, the amount of arzoxifene active per tablet was 10 mg, with the amount of cysteine hydrochloride (per tablet) for each lot respectively, being 0.0 mg, 0.1 mg and 0.5 mg. For tablet lots D, E and F, the amount of arzoxifene active per tablet was 20 mg, with the amount of cysteine hydrochloride (per tablet) for each lot respectively, being 0.0 mg, 0.5 mg and 0.75 mg. The unit formulae for each of these lots are summarized in Table 2 which includes the amounts (mg/tablet) and type of excipient utilized in each case. As seen from the table, the tablet cores for lots D, E, and F included the application of a film coat which was applied via an aqueous dispersion in a side-vented coating pan fitted to a commercial air-handling unit.

TABLE 2

Tablet Unit Formulae (mg/tablet)

| Ingredient | Lot A | Lot B | Lot C | Lot D | Lot E | Lot F |
|---|---|---|---|---|---|---|
| Arzoxifene HCl (Base Equivalent) | 11.31 (10) | 11.31 (10) | 11.31 (10) | 22.73 (20) | 22.73 (20) | 22.73 (20) |
| L-Cysteine HCl Monohydrate | — | 0.10 | 0.50 | — | 0.50 | 0.75 |
| Povidone | 12.50 | 12.50 | 12.50 | 12.50 | 12.50 | 12.50 |
| Polysorbate 80 | 1.25 | 1.25 | 1.25 | 1.25 | 1.25 | 1.25 |
| Anhydrous Lactose | 148.75 | 148.67 | 148.35 | 139.62 | 139.22 | 139.02 |
| Lactose Monohydrate | 37.19 | 37.17 | 37.09 | 34.90 | 34.80 | 34.75 |
| Crospovidone | 12.50 | 12.50 | 12.50 | 12.50 | 12.50 | 12.50 |
| Microcrystalline Cellulose | 25.00 | 25.00 | 25.00 | 25.00 | 25.00 | 25.00 |
| Magnesium Stearate | 1.50 | 1.50 | 1.50 | 1.50 | 1.50 | 1.50 |
| Color Mixture Yellow | — | — | — | 10.00 | 10.00 | 10.00 |

Following preparation of the respective formulations, the tablets were assayed for their levels of degradation products (N-oxide, cleavage product and total). Analysis for the arzoxifene N-oxide degradation product, the arzoxifene cleavage product and total related substances (process related impurities plus degradation products) was performed using a gradient HPLC method. The separation was performed using a 5 µm, 250×4.6 mm i.d. Inertsil® C8 column. The gradient elution utilized acetonitrile and a pH 3.0 phosphate buffer (6 g $KH_2PO_4$/L). The initial mobile phase composition was 30% acetonitrile/70% buffer (mobile phase A) and the final mobile phase composition was 70% acetonitrile/30% buffer (mobile phase B). Mobile phase B started at 0% and was increased linearly at a rate of 1.8% per minute for 20 minutes to 36% B. It was held at 36% for 25 minutes, increased at 6.4% per minute for 10 minutes to 100% B and held at 100% B for two minutes. The column temperature was maintained at 40° C., the mobile phase flow rate was 1.0 mL/minute and a 10 µL sample injection was used. Related substances for arzoxifene were monitored by UV detection at a wavelength of 310 nm and quantitated as percent of total peak area.

Additionally, tablets from each lot were stored in open dishes at controlled temperatures (40° C.) for 6 months. Throughout this storage period tablets were assayed (as described above) for the formation of degradation products (N-oxide, cleavage product and total). Data from these studies are summarized in tabular form in Table 3 and Table 4 for the 10 mg (A, B and C) and 20 mg strengths (D, E and F) respectively. The data indicate that the presence of cysteine hydrochloride at a level of 0.5 mg/tablet in both strengths of arzoxifene tablets, resulted in an order of magnitude reduction in the N-oxide level after 6 months storage at 40° C. relative to the formulation with no stabilizer. Increases in the level of the cleavage product were also significantly reduced by approximately a factor of two in the presence of cysteine hydrochloride compared to those lots which did not contain the stabilizer.

TABLE 3

Tablet Compositions of Arzoxifene (10 mg Strength)
Chemical Stability Data as A Function of Time
Open Dish Storage at 40° C.

| | Control Lot LOT A | Cysteine HCl 0.1 mg/tab LOT B | Cysteine HCl 0.5 mg/tab LOT C |
|---|---|---|---|
| Initial Timepoint | | | |
| N-oxide (%) | 0.00 | 0.00 | 0.00 |
| CDP (%) | 0.14 | 0.12 | 0.12 |
| TRS (%) | 1.12 | 1.08 | 1.08 |
| 2 Week Timepoint | | | |
| N-oxide (%) | 0.05 | 0.01 | 0.00 |
| CDP (%) | 0.19 | 0.14 | 0.13 |
| TRS (%) | 1.27 | 1.14 | 1.14 |
| 1 Month Timepoint | | | |
| N-oxide (%) | 0.09 | 0.03 | 0.00 |
| CDP (%) | 0.26 | 0.16 | 0.13 |
| TRS (%) | 1.55 | 1.27 | 1.18 |
| 3 Month Timepoint | | | |
| N-oxide (%) | 0.32 | 0.20 | 0.02 |
| CDP (%) | 0.34 | 0.26 | 0.15 |
| TRS (%) | 2.19 | 1.88 | 1.44 |
| 6 Month Timepoint | | | |
| N-oxide (%) | 0.55 | 0.34 | 0.06 |

TABLE 3-continued

Tablet Compositions of Arzoxifene (10 mg Strength)
Chemical Stability Data as A Function of Time
Open Dish Storage at 40° C.

|  | Control Lot LOT A | Cysteine HCl 0.1 mg/tab LOT B | Cysteine HCl 0.5 mg/tab LOT C |
|---|---|---|---|
| CDP (%) | 0.49 | 0.35 | 0.20 |
| TRS (%) | 3.02 | 2.66 | 2.03 |

N-oxide = Identified Oxidative Degradation Product of Arzoxifene
TRS = Total Related Substances
CDP = Cleavage Degradation Product

TABLE 4

Tablet Compositions of Arzoxifene (20 mg Strength)
Chemical Stability Data as A Function of Time
Open Dish Storage at 40° C.

|  | Control Lot LOT D | Cysteine HCl 0.5 mg/tab LOT E | Cysteine HCl 0.75 mg/tab LOT F |
|---|---|---|---|
| Initial Timepoint |  |  |  |
| N-oxide (%) | 0.01 | 0.00 | 0.00 |
| CDP (%) | 0.13 | 0.13 | 0.13 |
| TRS (%) | 1.21 | 1.11 | 1.12 |
| 1 Month Timepoint |  |  |  |
| N-oxide (%) | 0.04 | 0.00 | 0.00 |
| CDP (%) | 0.14 | 0.13 | 0.12 |
| TRS (%) | 1.27 | 1.15 | 1.13 |
| 2 Month Timepoint |  |  |  |
| N-oxide (%) | 0.06 | 0.00 | 0.00 |
| CDP (%) | 0.16 | 0.14 | 0.13 |
| TRS (%) | 1.35 | 1.19 | 1.15 |
| 3 Month Timepoint |  |  |  |
| N-oxide (%) | 0.08 | 0.00 | 0.00 |
| CDP (%) | 0.17 | 0.13 | 0.13 |
| TRS (%) | 1.30 | 1.16 | 1.14 |
| 6 Month Timepoint |  |  |  |
| N-oxide (%) | 0.14 | 0.00 | 0.00 |
| CDP (%) | 0.15 | 0.10 | 0.10 |
| TRS (%) | 1.33 | 1.12 | 1.11 |

N-oxide = Identified Oxidative Degradation Product of Arzoxifene
TRS = Total Related Substances
CDP = Cleavage Degradation Product

B. 5 mg Arzoxifene Formulation

Core tablets weighing approximately 125 mg and containing approximately 5 mg of arzoxifene as arzoxifene hydrochloride are manufactured and assayed in the same manner as the 10 mg and 20 mg formulations described directly above. The amount of cysteine hydrochloride is 0.25 mg per tablet as shown in Table 5. Tablets are stored in an open dish at controlled temperature (40° C.) for three months. Throughout this storage period, tablets are assayed (as described above) for the formation of degradation products (N-oxide, cleavage product, and total). Data from this study are summarized in Table 6.

TABLE 5

Tablet Unit Formula (mg/tablet)

| Ingredient | Lot G |
|---|---|
| Arzoxifene HCl | 5.62 |
| (Base Equiv.) | (5) |
| L-Cysteine HCl Monohydrate | 0.25 |
| Povidone | 6.25 |
| Polysorbate 80 | 0.63 |
| Anhydrous Lactose | 74.21 |
| Lactose Monohydrate | 18.55 |
| Crospovidone | 6.24 |
| Microcrystalline Cellulose | 12.50 |
| Magnesium Stearate | 0.75 |
| Color Mixture Yellow | — |

TABLE 6

Tablet Compositions of Arzoxifene (5 mg Strength)
Chemical Stability Data as A Function of Time
Open Dish Storage at 40° C.

|  | Cysteine HCl 0.25 mg/tab LOT G |
|---|---|
| Initial Timepoint |  |
| N-oxide (%) | 0.01 |
| CDP (%) | 0.02 |
| TRS (%) | 1.35 |
| 1 Month Timepoint |  |
| N-oxide (%) | 0.04 |
| CDP (%) | 0.05 |
| TRS (%) | 1.63 |
| 2 Month Timepoint |  |
| N-oxide (%) | 0.05 |
| CDP (%) | 0.06 |
| TRS (%) | 1.73 |
| 3 Month Timepoint |  |
| N-oxide (%) | 0.05 |
| CDP (%) | 0.07 |
| TRS (%) | 1.82 |

N-oxide = Identified Oxidative Degradation Product of Arzoxifene
TRS = Total Related Substances
CDP = Cleavage Degradation Product

Example of Methionine as a Stabilizer

Core tablets weighing approximately 250 mg and containing approximately 1 mg of arzoxifene as arzoxifene hydrochloride were prepared generally as follows. The arzoxifene hydrochloride, water soluble diluents (lactose monohydrate and anhydrous lactose), and a portion of the distintegrant (crospovidone) were blended in a high shear granulator. This blend was then wet massed in the high shear granulator with an aqueous solution of the povidone and polysorbate 80. In those formulations which contained the tested stabilizers (ascorbic acid or methionine), the stabilizer was also dissolved in the granulation solution and added during the wet mass step via the granulation solution. To maintain a constant tablet fill weight, the amount of lactose (lactose monohydrate and anhydrous lactose) was reduced corresponding to the amount of stabilizer added. Following a wet sizing step through a rotating impeller mill, the granules were dried using a fluid bed dryer. The dried granules were reduced to a suitable size with a rotating impeller mill. The remaining ingredients (microcrystalline cellulose, magnesium stearate, and the rest of crospovidone) were added to the dried granules and blended. This mixture was then compressed into round shaped tablets using a conventional rotary tablet press. Tablet lot H was a control lot which contained no stabilizer, while tablet lots I and J contained 0.2% and 0.4% w/w of methionine respectively, while tablet lots K and L contained 0.2% and 0.4% w/w ascorbic acid respectively. The unit formulae for each of these lots are summarized in Table 7 which includes the amounts (mg/tablet) and type of excipient utilized in each case.

TABLE 7

Tablet Unit Formulae (mg/tablet)

| Ingredient | Lot H | Lot I | Lot J | Lot K | Lot L |
|---|---|---|---|---|---|
| Arzoxifene HCl (Base Equivalent) | 1.12 (1.0) | 1.12 (1.0) | 1.12 (1.0) | 1.12 (1.0) | 1.12 (1.0) |
| Ascorbic Acid | — | — | — | 0.50 | 1.00 |
| Methionine | — | 0.50 | 1.00 | — | — |
| Povidone | 12.50 | 12.50 | 12.50 | 12.50 | 12.50 |
| Polysorbate 80 | 2.50 | 2.50 | 2.50 | 2.50 | 2.50 |
| Anhydrous Lactose | 155.90 | 155.50 | 155.10 | 155.50 | 155.10 |
| Lactose Monohydrate | 38.98 | 38.88 | 38.78 | 38.88 | 38.78 |
| Crospovidone | 12.50 | 12.50 | 12.50 | 12.50 | 12.50 |
| Microcrystalline Cellulose | 25.00 | 25.00 | 25.00 | 25.00 | 25.00 |
| Magnesium Stearate | 1.50 | 1.50 | 1.50 | 1.50 | 1.50 |

Following preparation of the respective formulations, the tablets were assayed for their levels of degradation products (N-oxide, cleavage product and total). The analytical methodology was the same as previously outlined in earlier examples. In addition to assaying the tablets after completion of the manufacturing process, tablets from each lot were stored in open dishes at a controlled temperatures (40° C.) for 1 month. After two weeks and one month storage at this condition, tablets were assayed (as described previously) for the formation of degradation products (N-oxide, cleavage product and total). Data from these studies are summarized in tabular form in Table 8.

TABLE 8

Tablet Compositions of Arzoxifene (1 mg Strength) Chemical Stability Data as A Function of Time Open Dish Storage at 40° C.

| | Control Lot LOT H | Methionine 0.2% w/w LOT I | Methionine 0.4% w/w LOT J | Ascorbic Acid 0.2% w/w LOT K | Ascorbic Acid 0.4% w/w LOT L |
|---|---|---|---|---|---|
| Initial Timepoint | | | | | |
| N-oxide (%) | 0.29 | 0.01 | 0.02 | 0.70 | 0.82 |
| CDP (%) | 0.05 | 0.05 | 0.05 | 0.05 | 0.06 |
| TRS (%) | 1.16 | 0.89 | 0.88 | 1.58 | 1.70 |
| 2 Week Timepoint | | | | | |
| N-oxide (%) | 2.27 | 0.83 | 0.69 | 4.42 | 4.81 |
| CDP (%) | 0.83 | 0.94 | 0.93 | 0.22 | 0.22 |
| TRS (%) | 4.83 | 3.51 | 3.36 | 5.98 | 6.42 |
| 1 Month Timepoint | | | | | |
| N-oxide (%) | 4.04 | 1.55 | 1.16 | 5.65 | 5.98 |
| CDP (%) | 1.52 | 1.65 | 1.57 | 0.33 | 0.31 |
| TRS (%) | 8.80 | 5.95 | 5.25 | 8.06 | 8.08 |

N-oxide = Identified Oxidative Degradation Product of Arzoxifene
TRS = Total Related Substances
CDP = Cleavage Degradation Product Relative to the control lot, the data indicate that the incorporation of methionine did impart a stabilizing effect on the formulation. Following manufacture of the tablets, the tablets with methionine had significantly reduced levels of N-oxide degradation product with 0.01% and 0.02% for the 0.2% and 0.4% w/w methionine lots, relative to the control lots which had an N-oxide level of 0.29%. A similar trend was observed after storage at 40° C. for the N-oxide, with a corresponding decrease in the total related substances for the methionine containing lots relative to the control lot. Unlike cysteine hydrochloride, the methionine appeared to have little impact on the formation of the cleavage degradation product relative to the control lot.

In contrast, the incorporation of the classical stabilizer, ascorbic acid, actually augmented the formation of the N-oxide degradation product, both after manufacture and after storage at 40° C. relative to the control lot. After tablet manufacture, the level of total related substances was higher in the two tablet lots with incorporated ascorbic acid (0.2 and 0.4% w/w) relative to the control lot and the product developed a light pink discoloration. While the ascorbic acid did have some beneficial effect in reducing the level of the cleavage degradation product relative to control after storage at 40° C., the overall effect was negative given the impact on N-oxide, total related substances, and product discoloration.

Utilities

The terms "inhibiting" and "inhibit" include their generally accepted meaning, i.e., preventing, prohibiting, restraining, alleviating, ameliorating, slowing, stopping, or reversing the progression or severity of a pathological condition, or sequela thereof, described herein.

The terms "preventing", "prevention of", "prophylaxis", "prophylactic" and "prevent" are used herein interchangeably and refer to reducing the likelihood that the recipient of the stabilized formulation will incur or develop any of the pathological conditions, or sequela thereof, described herein.

The term "estrogen deprived" refers to a condition, either naturally occurring or clinically induced, where a woman can not produce sufficient estrogenic hormones to maintain estrogen dependent functions, e.g., menses, homeostasis of bone mass, neuronal function, cardiovascular condition, etc. Such estrogen deprived situations arise from, but are not limited to, menopause and surgical or chemical ovarectomy, including its functional equivalent, e.g., medication with GnRH agonists or antagonists, ICI 182780, and the like.

U.S. Pat. Nos. 5,510,357 and 5,723,474 specifically teach that arzoxifene is useful for, inter alia, lowering serum cholesterol and for inhibiting hyperlipidemia, osteoporosis, estrogen dependent cancers including breast and uterine cancers, endometriosis, aortal smooth muscle cell proliferation, and restenosis. The compound is currently undergoing clinical evaluation for the treatment and prevention of osteoporosis and the treatment of endometrial and breast cancer in women.

As related above, arzoxifene is also useful for, and is being clinically evaluated for the treatment of receptor positive metastatic breast cancer; the adjuvant treatment of receptor positive patients following appropriate local or systemic therapy; the reduction of recurrence of invasive and noninvasive breast cancer; the reduction of the incidence of invasive breast cancer and ductal carcinoma in situ ("DCIS"). The stabilized formulations of arzoxifene as disclosed herein are likewise useful for the above indications.

In addition, arzoxifene is also useful in the inhibition of the above indications in combination with appropriate radiotherapy; and/or an effective amount of aromatase inhibitors; LHRH analogues; and/or acetylcholinesterase inhibitors.

Regarding aromatase inhibitors, by definition, the ovaries of a postmenopausal woman are not functioning. Her only source of estrogen is through conversion of adrenal androgens to estrogens by the enzyme aromatase, which is found in peripheral tissues (including fat, muscle and the breast tumor itself). Thus, drugs that inhibit aromatase (aromatase inhibitors) deplete the postmenopausal woman of circulating estrogen. Estrogen deprivation by means of aromatase inhibition is an important treatment option for patients with metastatic breast cancer. Various aromatase inhibitors are commercially available. Aromatase inhibitors include, for example, Aminoglutemide (CYTANDREN®) (250–1250 mg/day, preferably 250 mg four times per day), Anastrazole (ARIMIDEX®)(1–5 mg/day, preferably 1 mg once per day), Letrozole (FEMARA®)(2.5–10 mg/day, preferably 2.5 mg once a day), Formestane (LENATRON®) (250–1250 mg per week, preferably 250 mg twice weekly), Exemestane (AROMASIN®) (25–100 mg/day, preferably 25 mg once per day), and the like.

As for LHRH analogues, continuous exposure to the LHRH (lutenizing hormone releasing hormone) analogues inhibits estrogen production in the premenopausal women by desensitizing the pituitary gland, which then no longer stimulates the ovaries to produce estrogen. The clinical effect is a "medical oophrectomy" which is reversible upon cessation of the LHRH analogue. LHRH analogues include, for example, Goserlin (ZOLADEX®) (3–15 mg/three months, preferably 3.6–7.2 mg once every three months), Leuprolide (LUPRON®) (3–15 mg/month, preferably 3.75–7.5 mg once every month), and the like.

Selected Testing Procedures

Uterine Fibrosis Test Procedures

Methods of the current invention for the inhibition of uterine fibrosis may be demonstrated by means of the following procedures.

Test 1

Between 3 and 20 women having uterine fibrosis are administered the stabilized formulation disclosed herein. The amount of arzoxifene administered is from 1 to 100 mg/day, and the period of administration is 3 months. The women are observed during the period of administration, and up to 3 months after discontinuance of administration, for effects on uterine fibrosis.

Test 2

The same procedure is used as in Test 1, except the period of administration is 6 months.

Test 3

The same procedure is used as in Test 1, except the period of administration is 1 year.

Alzheimer's Disease Test Procedures

Methods of the current invention for the treatment or prevention of Alzheimer's disease, especially in post-menopausal women, may be demonstrated by means of the following procedures.

Ten to fifty women are selected for a clinical study. The selection criteria are: at least one year post-menopausal, in reasonable good health, and have been diagnosed with early stages Alzheimer's Disease (AD). Further, these patients are staged in their disease, such that there is a good expectation that during the course of the study, most patients will experience a marked increase in the severity of pathologic symptoms. The patients are divided into two groups, one group is given a placebo, while the test group is given the stabilized formulation disclosed herein. The amount of arzoxifene administered is from 1 to 100 mg/day, once a day. The study is continued for six to thirty-six months in duration. All patients are given a complete mental profile at the beginning, each six months, and at termination of the study. This profile, used to evaluated the extent of the disease, includes capacity factors such as memory, cognition, reasoning ability, self-sufficiency, and the like. Also, included in the patient evaluation are objective parameters such as changes in brain structure as measured by CAT scanning techniques. Such methodologies and mental evaluations may be found in many standard texts on the subject. The results are compared both between groups at various time points and the changes in each patient versus time. A positive result is demonstrated by an inhibition in the type or severity of the degenerative symptoms in the test group given a formulation of the present invention, in contrast to those patients given the placebo.

We claim:

1. A pharmaceutical formulation comprising 6-hydroxy-3-(4-[2-(piperidin-1-yl)ethoxy]phenoxy)-2-(4-methoxyphenyl)benzo[b]thiophene or a salt thereof; a stabilizing agent selected from methionine, acetylcysteine, cysteine or salts thereof in an amount sufficient to effect stabilization to decomposition; and pharmaceutically acceptable excipients.

2. A pharmaceutical formulation according to claim 1 wherein the stabilizing agent is present in said formulation in an amount of from about 0.01 to about 10 percent by weight of the total formulation.

3. A pharmaceutical formulation according to claim 2 wherein the stabilizing agent is present in said formulation in an amount of from about 0.05 to about 5.0 percent by weight of the total formulation.

4. A pharmaceutical formulation according to claim 3 wherein the 6-hydroxy-3-(4-[2-(piperidin-1-yl)ethoxy]phenoxy)-2-(4-methoxyphenyl)benzo[b]thiophene is present as 6-hydroxy-3-(4-[2-(piperidin-1-yl)ethoxy]phenoxy)-2-(4-methoxyphenyl)benzo[b]thiophene hydrochloride.

5. A pharmaceutical formulation according to claim 4 wherein said 6-hydroxy-3-(4-[2-(piperidin-1-yl)ethoxy]phenoxy)-2-(4-methoxyphenyl)benzo[b]thiophene hydrochloride is crystalline 6-hydroxy-3-(4-[2-(piperidin-1-yl)ethoxy]phenoxy)-2-(4-methoxyphenyl)benzo[b]thiophene hydrochloride hydrate (F-I) having an X-ray diffraction d line spacing pattern which comprises the following peaks: 7.91±0.2, 10.74±0.2, 14.86±0.2, 15.92±0.2, 18.28±0.2, and 20.58±0.2° in 2θ; when obtained from a copper radiation source.

6. A pharmaceutical formulation according to claim 4 wherein said 6-Hydroxy-3-(4-[2-(piperidin-1-yl)ethoxy]phenoxy)-2-(4-methoxyphenyl)benzo[b]thiophene hydrochloride is crystalline 6-hydroxy-3-(4-[2-(piperidin-1-yl)ethoxy]phenoxy)-2-(4-methoxyphenyl)benzo[b]thiophene hydrochloride hydrate (F-III) having an X-ray diffraction d line spacing pattern which comprises the following peaks: 4.63±0.2, 7.82±0.2, 9.29±0.2, 13.97±0.2, 17.62±0.2, 20.80±0.2, and 24.31±0.2° in 2θ; when obtained at 25±2° C. and 35±10% relative humidity from a copper radiation source.

7. A pharmaceutical formulation according to claim 4 wherein said 6-Hydroxy-3-(4-[2-(piperidin-1-yl)ethoxy]phenoxy)-2-(4-methoxyphenyl)benzo[b]thiophene hydrochloride is crystalline 6-hydroxy-3-(4-[2-(piperidin-1-yl)ethoxy]phenoxy)-2-(4-methoxyphenyl)benzo[b]thiophene hydrochloride hydrate (F-V) having an X-ray diffraction pattern which comprises at least one of the following peaks: 7.3±0.2, 15.5±0.2, 15.9±0.2, and 17.6±0.2° in 2θ when obtained from a copper radiation source.

8. A pharmaceutical formulation according to claim 7 wherein said X-ray diffraction pattern further comprises the following peaks: 17.9±0.2, 18.2±0.2, 18.9±0.2, and 21.5±0.2° in 2θ when obtained from a copper radiation source.

9. A pharmaceutical formulation according to claim 4 wherein the stabilizing agent is cysteine, or a salt thereof.

10. A pharmaceutical formulation according to claim 4 wherein the stabilizing agent is cysteine hydrochloride.

11. A pharmaceutical formulation according to claim 4 wherein the stabilizing agent is L-cysteine hydrochloride monohydrate.

12. A pharmaceutical formulation according to claim 4 wherein the stabilizing agent is methionine, or a salt thereof.

13. A pharmaceutical formulation according to claim 4 wherein the stabilizing agent is acetylcysteine, or a salt thereof.

14. A pharmaceutical formulation according to claim 4 which is a tablet.

15. A pharmaceutical formulation according to claim 4 which is a capsule.

16. A pharmaceutical formulation according to claim 10 containing approximately 21.53 mg of 6-hydroxy-3-(4-[2-(piperidin-1-yl)ethoxy]phenoxy)-2-(4-methoxyphenyl)benzo[b]thiophene hydrochloride, and approximately 0.5 mg of cysteine hydrochloride.

17. A pharmaceutical formulation according to claim 16 which is a tablet weighing approximately 250 mg.

18. A pharmaceutical formulation according to claim 10 containing approximately 5.62 mg of 6-hydroxy-3-(4-[2-(piperidin-1-yl)ethoxy]phenoxy)-2-(4-methoxyphenyl)benzo[b]thiophene hydrochloride, and approximately 0.25 mg of cysteine hydrochloride.

19. A pharmaceutical formulation according to claim 18 which is a tablet weighing approximately 125 mg.

20. A pharmaceutical formulation according to claim 16 wherein the cysteine hydrochloride is L-cysteine hydrochloride monohydrate.

21. A method of treading a pathological condition selected from the group consisting of: endometriosis, breast cancer, and osteoporosis; which comprises administering to a mammal in need thereof, an effective amount of the pharmaceutical formulation of claim 1.

22. The method of claim 21 wherein the pathological condition is breast cancer.

23. The method of claim 21 wherein the pathological condition is osteoporosis.

24. The method of claim 21 wherein the pathological condition is endometrial cancer.

25. A method of stabilizing a pharmaceutical formulation comprising 6-hydroxy-3-(4-[2-(piperidin-1-yl)ethoxy]phenoxy)-2-(4-methoxyphenyl)benzo[b]thiophene or a salt thereof to decomposition which method comprises incorporation into said pharmaceutical formulation, in addition to a therapeutically effective amount of said 6-hydroxy-3-(4-[2-(piperidin-1-yl)ethoxy]phenoxy)-2-(4-methoxyphenyl)benzo[b]thiopene or a salt thereof and one or more pharmaceutically acceptable excipients, a stabilizing agent selected from methionine, acetycysteine, cysteine, or salts thereof in an amount sufficient to effect stabilization to decomposition.

26. A method of claim 25 wherein the 6-hydroxy-3-(4-[2-(piperidin-1-yl)ethoxy]phenoxy)-2-(4-methoxyphenyl)benzo[b]thiophene is present as 6-hydroxy-3-(4-[2-(piperidin-1-yl)ethoxy]phenoxy)-2-(4-methoxyphenyl)benzo[b]thiophene hydrochloride.

27. A method according to claim 26 wherein the stabilizing agent is present in said formulation in an amount of from about 0.01 to about 10 percent by weight of the total formulation.

28. A method according to claim 27 wherein the stabilizing agent is cysteine.

29. A method according to claim 27 wherein the stabilizing agent is cysteine hydrochloride.

30. A method according to claim 29 wherein the cysteine hydrochloride is L-cysteine hydrochloride monohydrate.

31. A method according to claim 27 wherein the stabilizing agent is methionine.

32. A method according to claim 27 wherein the stabilizing agent is acetyleysteine.

33. Use of crystalline 6-hydroxy-3-(4-[2-(piperidin-1-yl)ethoxy]phenoxy)-2-(4-methoxyphenyl)benzo[b]thiophene hydrochloride hydrate (F-I) having an X-ray diffraction d line spacing pattern which comprises the following peaks: 7.91±0.2, 10.74±0.2, 14.86±0.2, 15.92±0.2, 18.28±0.2, and 20.58±0.2° in 2θ; when obtained from a copper radiation source, in the manufacture of a medicament for the treatment of uterine fibrosis, endometriosis, aortal smooth muscle cell proliferation, restenosis, breast cancer, uterine cancer, prostatic cancer or benign prostatic hyperplasia, bone loss, osteoporosis, cardiovascular disease, hyperlipidemia, CNS disorders or Alzheimer's disease.

34. A pharmaceutical formulation according to claim 3 wherein the stabilizing agent is cysteine, or a salt thereof.

35. A pharmaceutical formulation according to claim 34 wherein the stabilizing agent is cysteine hydrochloride.

36. A pharmaceutical formulation according to claim 35 wherein the stabilizing agent is L-cysteine hydrochloride monohydrate.

37. A pharmaceutical formulation according to claim 3 wherein the stabilizing agent is methionine, or a salt thereof.

38. A pharmaceutical formulation according to claim 3 wherein the stabilizing agent is acetyleysteine, or a salt thereof.

39. A pharmaceutical formulation according to claim 18 wherein the cysteine hydrochloride is L-cysteine hydrochloride monohydrate.

* * * * *